US011898091B2

(12) United States Patent
Leinweber et al.

(10) Patent No.: US 11,898,091 B2
(45) Date of Patent: *Feb. 13, 2024

(54) SYNERGISTIC BLENDS OF ANTI-AGGLOMERANT GAS HYDRATE INHIBITORS WITH QUATERNARY BENZYL AMMONIUM COMPOUNDS

(71) Applicant: Clariant International, Ltd., Muttenz (CH)

(72) Inventors: Dirk Leinweber, Kelkheim (DE); Zachary Thomas Ward, Spring, TX (US); Felix Hoevelmann, Mühldorf (DE); Jonathan James Wylde, The Woodlands, TX (US); Matthias Krull, Harxheim (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/099,233

(22) Filed: Nov. 16, 2020

(65) Prior Publication Data
US 2021/0179918 A1 Jun. 17, 2021

Related U.S. Application Data

(60) Provisional application No. 62/946,679, filed on Dec. 11, 2019.

(51) Int. Cl.
C09K 8/52 (2006.01)
C10L 1/222 (2006.01)
C10L 3/10 (2006.01)
C07D 207/404 (2006.01)

(52) U.S. Cl.
CPC ............ *C09K 8/52* (2013.01); *C07D 207/404* (2013.01); *C10L 1/2222* (2013.01); *C10L 3/107* (2013.01); *C09K 2208/22* (2013.01)

(58) Field of Classification Search
CPC ...... C09K 8/52; C09K 2208/22; C09K 8/524; C09K 8/035; C07D 207/404; C10L 1/2222; C10L 3/107; C10L 2200/0259
See application file for complete search history.

(56) References Cited

U.S. PATENT DOCUMENTS

| | | |
|---|---|---|
| 4,832,871 A | 5/1989 | Bade |
| 4,915,176 A | 4/1990 | Sugier |
| 4,973,775 A | 11/1990 | Sugier |
| 5,244,878 A | 9/1993 | Sugier |
| 5,460,728 A | 10/1995 | Klomp |
| 5,648,575 A | 7/1997 | Klomp |
| 5,879,561 A | 3/1999 | Klomp |
| 6,015,929 A | 1/2000 | Rabeony |
| 6,369,004 B1 | 4/2002 | Klug |
| 6,596,911 B2 | 7/2003 | Przybylinski |
| 7,381,689 B2 | 6/2008 | Panchalingam |
| 9,765,254 B2 | 9/2017 | Lucente-Schultz |
| 10,870,789 B2 | 12/2020 | Pou |
| 2004/0163306 A1 | 8/2004 | Dahlmann |
| 2004/0167040 A1 | 8/2004 | Dahlmann |
| 2005/0081432 A1 | 4/2005 | Panchalingam |
| 2005/0101495 A1 | 5/2005 | Dahlmann |
| 2006/0237691 A1 | 10/2006 | Meier |
| 2007/0079963 A1 | 4/2007 | Yang |
| 2009/0042749 A1 | 2/2009 | Meier |
| 2009/0173663 A1 | 7/2009 | Leinweber |
| 2010/0087339 A1* | 4/2010 | Acosta ...................... C10L 3/10 507/90 |
| 2010/0116642 A1 | 5/2010 | Krull |
| 2014/0021262 A1 | 1/2014 | Matsumura |
| 2014/0091262 A1* | 4/2014 | Webber ................. C23F 11/145 252/392 |
| 2016/0122619 A1* | 5/2016 | Lucente-Schultz ...... C09K 8/52 507/90 |
| 2016/0186039 A1 | 6/2016 | Owsik |
| 2017/0305838 A1 | 10/2017 | Appel |
| 2018/0030340 A1 | 2/2018 | McCabe |
| 2018/0333339 A1 | 11/2018 | Hamersky |
| 2018/0346790 A1 | 12/2018 | Pou |
| 2018/0346791 A1 | 12/2018 | Bartels |

FOREIGN PATENT DOCUMENTS

| | | |
|---|---|---|
| CN | 101906293 | 12/2010 |
| CN | 105733539 | 7/2016 |
| EP | 0651049 | 5/1995 |
| GB | 2349889 | 11/2000 |
| GB | 2542656 A | 3/2017 |
| WO | 2002066785 | 8/2002 |
| WO | 2005042675 | 5/2005 |

(Continued)

OTHER PUBLICATIONS

International Preliminary Report on Patentability for App. No. PCT/EP2020/084719, dated May 17, 2022, 8 pages.

(Continued)

*Primary Examiner* — Kumar R Bhushan

(57) ABSTRACT

Disclosed is a gas hydrate inhibitor composition comprising an amphiphile by a linking moiety, the amphiphile having of the general formula (1)

$$[R^5\text{-L-N}(R^1)(R^2)(R^3)]^+X^- \quad (1)$$

wherein
each of $R^1$ and $R^2$ is an alkyl group having from 1 to 5 carbon atoms;
or wherein the nitrogen atom and the $R^1$ and $R^2$ groups together form a heterocyclic group;
$R^3$ is present or not as hydrogen or an alkyl group having from 1 to 8 carbon atoms
L is a linking moiety comprising a hydrocarbyl group having at least 2 adjacent carbon atoms, at least one heteroatom selected from nitrogen and oxygen,
$R^5$ is a hydrocarbyl group having from 6 to 22 carbon atoms; and
X– is present as an anion when $R^3$ is present;
and a cationic surfactant which is selected from quaternary benzyl ammonium salts and a method of using the gas hydrate inhibitor composition.

31 Claims, No Drawings

(56) References Cited

FOREIGN PATENT DOCUMENTS

| WO | 2006072083 | 7/2006 |
|---|---|---|
| WO | 2012082815 | 6/2012 |
| WO | 2012102916 | 8/2012 |
| WO | 2013089802 | 6/2013 |
| WO | 2016069987 | 5/2016 |
| WO | 2017089724 | 6/2017 |
| WO | 2017184115 | 10/2017 |
| WO | 2017223306 | 12/2017 |
| WO | 2018115186 | 6/2018 |
| WO | 2019015828 | 1/2019 |

OTHER PUBLICATIONS

International Search Report for App. No. PCT/EP2020/084718, dated Mar. 4, 2021, 2 pages.
International Search Report for App. No. PCT/EP2020/084719, dated Mar. 4, 2021, 3 pages.
International Search Report for App. No. PCT/EP2020/084722, dated Mar. 4, 2021, 3 pages.
International Search Report for App. No. PCT/EP2020/084726, dated Mar. 4, 2021, 3 pages.
International Search Report and Written Opinion for App. No. PCT/EP2020/084717, dated Mar. 3, 2021, 14 pages.
International Search Report and Written Opinion for App. No. PCT/EP2020/084721, dated Mar. 4, 2021, 16 pages.
International Search Report and Written Opinion for App. No. PCT/EP2020/084724, dated Mar. 4, 2021, 16 pages.
International Search Report for App. No. PCT/EP2019/074182 dated Dec. 6, 2019, 4 pages.
Khan (M. S. Khan et al, Tetramethyl ammonium chloride as dual functional inhibitor for methane and carbon dioxide hydrates, Fuels 2019, 236, 251-263).
M. Sun, et al., J. Colloid Interf. Sci., 402 (2013), pp. 312-319.
Machine translation of CN101906293, Aug. 12, 2010, 24 pages.
Product data sheet for TetraMethylAmmonium Chloride, downloaded on Jan. 29, 2022, 8 pages.
Whitmore et al., "Basically Substituted Aliphatic Nitriles and their Catalytic Reduction to Amines", Jornal of American Chemical Society, vol. 66, May 1944, pp. 725-731.

* cited by examiner

SYNERGISTIC BLENDS OF ANTI-AGGLOMERANT GAS HYDRATE INHIBITORS WITH QUATERNARY BENZYL AMMONIUM COMPOUNDS

CROSS REFERENCE TO RELATED APPLICATION

This application claims priority to U.S. Provisional Patent Application No. 62/946,679, filed Dec. 11, 2019, the entirety of which is hereby incorporated herein by reference.

This invention relates to the prevention of gas hydrate blockage in oil and natural gas pipelines containing low-boiling point hydrocarbons and water. More specifically, the invention relates to a method of controlling gas hydrate blockage through the addition of a synergistically acting blend of chemical compositions.

Gas hydrates are typically solids that may form in a fluid that is flowing or is substantially stationary, under certain temperature and pressure conditions. For example, gas hydrates may form during hydrocarbon production from a subterranean formation, in pipelines and other equipment during production operations. Hydrates may impede or completely block flow of hydrocarbons or other fluid flowing through such pipelines. These blockages not only may decrease or stop production, potentially costing millions of dollars in lost production, but also may be very difficult and dangerous to mediate. Unless properly handled, gas hydrates may be volatile and even explosive, potentially rupturing pipelines, damaging equipment, endangering workers, and causing environmental harm. Gas hydrates may form when water molecules become bonded together after coming into contact with certain "guest" gas or liquid molecules. Hydrogen bonding may cause the water molecules to form a regular lattice structure, like a cage, that is stabilized by the guest gas or liquid molecules entrapped within the lattice structure. The resulting crystalline structure may precipitate as a solid gas hydrate. Guest molecules can include any number of molecules such as, for example, carbon dioxide hydrogen, and low molecular weight hydrocarbons including methane, ethane, propane, n-butane, iso-butane, n-pentane, iso-pentane, and the like, and combinations of these gases as for example natural gas.

There are two basic techniques to overcome or control the gas hydrate problems, namely thermodynamic and low dose hydrate inhibitors (LDHIs). Thermodynamic hydrate inhibitors, such as methanol or one of the glycols, have traditionally been used to prevent these hydrate formations. These thermodynamic inhibitors are effective at 5-50% (or higher) based on the amount of water. As oil companies are exploring new production in deep waters, the total gas/oil/water productions are also increasing. The use of thermodynamic inhibitors is not viable in these applications due to logistical constraints of supplying and pumping such vast quantities of fluids to often remote locations.

LDHIs can overcome such logistical constraints. There are two broad categories of LHDI: Kinetic Hydrate Inhibitors (KHIs) and Anti-Agglomerants (AAs). Kinetic hydrate inhibitors have been identified to prevent hydrate formation so that the fluids can be pumped out before a catastrophic hydrate formation occurs. The kinetic inhibitors prevent or delay hydrate crystal nucleation and disrupt crystal growth. Kinetic hydrate inhibitors contain moieties similar to gas molecules previously mentioned. It is believed that kinetic inhibitors impede hydrate crystal growth by becoming incorporated into the growing hydrate crystals, thereby disrupting further hydrate crystal growth. The growing hydrate crystals can complete a cage by combining with the partial hydrate-like cages around the kinetic hydrate inhibitor moieties containing hydrate-like groups. KHIs are effective with or without the presence of a liquid hydrocarbon phase, but they are typically less effective in preventing hydrate formation as the production pressure increases. Examples of kinetic hydrate inhibitors include poly(N-methylacrylamide), poly(N,N-dimethylacrylamide), poly(N-ethylacrylamide), poly(N,N-diethylacrylamide), poly(N-methyl-N-vinylacetamide), poly(2-ethyloxazoline), poly(N-vinylpyrrolidone), poly(N-vinylcaprolactam), and copolymers comprising the respective monomers.

Besides the kinetic hydrate inhibitors, there is a second general type of LDHIs, the so-called anti-agglomerants. While KHIs work by delaying or even preventing the growth of gas hydrate crystals and may function as "anti-nucleators", anti-agglomerants allow hydrates to form but disperse them in the form of fine particles, known as a hydrate slurry. AAs prevent hydrates from agglomeration and subsequently from accumulating into larger aggregates capable of causing plugs. Often anti-agglomerants prevent the once formed smaller gas hydrate crystals to adhere to the pipe wall.

Unlike the kinetic hydrate inhibitors, anti-agglomerants are effective only in the presence of an oil phase. The oil phase provides a transport medium for the hydrates which are referred to as hydrate slurries so that the overall viscosity of the medium is kept low and can be transported along the pipeline. As such, the hydrate crystals formed in the water-droplets are prevented from agglomerating into a larger crystalline mass.

A group of chemicals which has proven to prevent agglomeration of hydrate crystals are quaternary ammonium salts having at least three alkyl groups with four or five carbon atoms and a long chain hydrocarbon group containing 8-20 atoms, as for example tributylhexadecylphosphonium bromide and tributylhexadecylammonium bromide.

Accordingly, U.S. Pat. No. 5,460,728 teaches a method for inhibiting the formation of hydrates, the method including the addition of alkylated ammonium, phosphonium or sulphonium compounds having three or four alkyl groups in their molecule, at least three of which are independently chosen from the group of normal or branched alkyls having at least four and preferably four to six carbon atoms to a stream containing low-boiling hydrocarbons and water. While tributyldecylammoniumbromide shows excellent performance, methyl analogues as for example trimethyldodecylammoniumbromide are ineffective.

Similarly, U.S. Pat. No. 5,648,575 teaches a method for inhibiting the plugging of a conduit, the method including the addition of alkylated ammonium, phosphonium or sulphonium compounds having three or four substituents in their molecule, at least two of which are independently chosen from the group of normal or branched alkyls having at least four carbon atoms and the third is an organic moiety having at least 4 atoms to a stream containing low-boiling hydrocarbons and water.

U.S. Pat. No. 5,879,561 teaches a method for inhibiting the plugging of a conduit, the method including the addition of alkylated ammonium or phosphonium compounds having four alkyl groups, two of which are independently normal or branched alkyls having four or five carbon atoms and two more of which independently represent organic moieties having at least eight carbon atoms as for example in dibutyldicocoyl ammonium bromide, to a stream containing hydrocarbons having from 1 to 8 carbon atoms and water.

WO 02/066785 discloses a method for inhibiting formation of hydrocarbon hydrates, comprising contacting a composition comprising an onium compound and an amine salt with a mixture comprising water and a hydrocarbon. The onium compound comprises two groups selected from normal or branched alkyls containing a chain of at least 4 carbon atoms, and an organic moiety containing a chain of at least 4 carbon atoms. For ammonium compounds, the fourth residue is selected from H, an alkyl, aryl, alkylaryl, alkenylaryl or alkenyl group, preferably having from about 1 to about 20 carbon atoms. This includes for example dibutyldidodecylammonium salts. The amine salts include amines with a total of twelve or fewer, preferably nine or fewer, carbon atoms in a particular molecule, being neutralized with a lower carboxylic acid having four or fewer carbon atoms and inorganic acids.

U.S. Pat. No. 6,369,004 teaches the kinetic inhibition of gas hydrate formation using polymers based on reacting maleic anhydride with one or more amines. These polymers can also be used together with various other substances, called synergists, including tetrabutylammonium salts, tetrapentylammonium salts, tributylamine oxide, tripentylamine oxide, zwitterionic compounds having at least one butyl or pentyl group on the quaternary ammonium nitrogen atom, such as $Bu_3N^+$—$CH_2$—$COO^-$. However, kinetic inhibitors are not effective as the pipeline pressure increases.

Another group of chemicals which has proven to efficiently prevent agglomeration of hydrate crystals are amphiphilic carboxylic acid derivatives comprising a lipophilic alkyl chain and a tertiary amino group respectively an ammonium group.

WO 2012/082815 discloses compositions comprising beta-amino ester surfactants and their ammonium salts as anti-agglomerants. The beta-amino ester surfactants can be made by nucleophilic addition of a 3-(dialkylamino)-propylamine to an acrylic acid ester and subsequent neutralization of the amino group with a mineral acid or a carboxylic acid, respectively quaternization of the amino group.

WO 2013/089802 discloses compositions comprising salts of beta-amino amide surfactants and their use as anti-agglomerants to reduce or inhibit the formation of gas hydrates. The beta-amino amides can be made by nucleophilic addition of an amine as for example dibutyl amine to acrylic acid followed by amidation with a fatty amine and subsequent neutralization of the amino group with a mineral acid or a carboxylic acid, respectively quaternization.

WO 2016/069987 discloses hydrate inhibitor compositions comprising zwitterionic or cationic ammonium surfactants. The hydrate inhibitors may be made by reaction of acrylic acid with a fatty amine and a N,N-dialkylaminoalkyl amine, followed by quaternization or neutralization of the amino group.

WO 2017/184115 discloses compositions and methods of using these compositions to inhibit of the formation of gas hydrate agglomerates wherein the compositions may be characterized as reaction products of: (1) a dialkylaminoalkyl amine and (2) a first intermediate formed as the reaction product of one or more unsaturated carboxylic acids or esters containing an alkene chain (e.g., acrylates) and an amine that may further be reacted with (3) one or more alkylating agents.

U.S. Pat. No. 7,381,689 teaches a method and an amide composition used therein for inhibiting, retarding, mitigating, reducing, controlling and/or delaying formation of hydrocarbon hydrates or agglomerants of hydrates in a process stream. The method comprises the addition of at least one amide compound into the process stream, where the compound may be mixed with another compound selected from amino alcohols, esters, quaternary ammonium, phosphonium or sulphonium salts, betaines, amine oxides, other amides, simple amine salts, and combinations thereof.

However, there remains a need for hydrate inhibitors that effectively prevent agglomeration of hydrates in oil and gas transportation and handling processes. It would be desirable to identify hydrate inhibitors that are effective at lower dosages, and that are especially effective at high pressures and/or low temperatures such as those encountered in deep water production and/or at high water cuts.

Furthermore, as most gas hydrate inhibitors are amphiphilic substances, they have potential to emulsify oil in the co-produced water which often has a negative impact on the operational system to which they are applied. Accordingly, emulsion tendency is an important secondary property, because the co-produced fluids (oil to be sold and water to be disposed of) need to separate quickly once topside, typically within 30 minutes, if not preferably less time as for example within 10 and even more preferred within 5 minutes. Separation speed is critical because if it is not fast enough, it may cause production to be choked back to allow time for the separation to occur; oil wetness must be minimized because there are typically limits to the amount of water that can remain in the salable oil, and finally, the produced water has a low limit to the amount of oil that can remain in it, in large part due to its eventual disposal overboard, back into the environment.

Surprisingly, it has been found that the performance of a gas hydrate inhibitor composition comprising an amphiphile which has a N,N-dialkylamino group linked to a hydrophobic tail via a linking moiety which is an optionally substituted hydrocarbyl group comprising at least one nitrogen and/or oxygen atom, will be synergistically enhanced in its performance as a gas hydrate inhibitor when used together with a cationic surfactant. Accordingly, such combination allows for reduced overall treat rates. Additionally, such combination provides further unexpected performance benefits which also have a beneficial effect on the operational system to which the gas hydrate inhibitors are applied, including less issues caused by foam formation and produced water quality. Specifically, such combination was found to result in improved water drop properties, including a reduction of the time to achieve significant water drop and a reduction of the absolute amount of water remaining emulsified into the co-produced oil. This reduces the need for further chemical treatment to separate emulsified water out of the oil prior to its export in the limited amount of time available once fluids are topside and need to be processed and often makes further chemical treatment unnecessary. Furthermore, it has been found that such combination is able to work at higher water cuts than previously possible with single use of hydrate inhibitor, i.e. the combination of the amphiphile with the cationic surfactant extends the range of water cuts that are possible to be treated for hydrate formation.

In a first aspect, the instant invention provides a gas hydrate inhibitor composition comprising
A) from 5 to 95 weight-% of an amphiphile having a hydrophobic tail linked to a hydrophilic head group by a linking moiety, the amphiphile having the general formula (1)

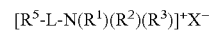  (1)

wherein
each of $R^1$ and $R^2$ is independently an alkyl group having from 1 to 5 carbon atoms; or wherein the nitrogen atom and the $R^1$ and $R^2$ groups together form a substituted or unsubstituted heterocyclic group;

$R^3$ is present or not as hydrogen or an alkyl group having from 1 to 8 carbon atoms which optionally bears a hydroxy group or a carboxy group in the 2-position;

L is a linking moiety comprising an optionally substituted hydrocarbyl group having at least 2 adjacent carbon atoms, at least one heteroatom selected from nitrogen and oxygen, and optionally one or more further heteroatoms;

$R^5$ is a hydrocarbyl group having from 6 to 22 carbon atoms; and $X^-$ is present as an anion when $R^3$ is present;

B) from 5 to 95 weight-% of a cationic surfactant which is selected from quaternary benzyl ammonium salts having besides the benzyl group at least one $C_8$-$C_{18}$-alkyl group bound to the nitrogen atom.

In a second aspect, the instant invention provides a method for inhibiting the formation of gas hydrate agglomerates and/or plugs, the method comprising bringing a system containing hydrocarbons and water susceptible to gas hydrate formation in contact with the composition according to the first aspect of the invention.

In a third aspect, the instant invention provides the use of the composition according to the first aspect of the invention for inhibiting the formation of gas hydrate agglomerates and/or plugs in a system containing hydrocarbons and water.

In a fourth aspect, the instant invention provides a method for improving the hydrate inhibitor performance of an amphiphile (A) having the general formula (1) given above, the method comprising the addition of a cationic surfactant (B) which is selected from quaternary benzyl ammonium salts having a benzyl group and at least one $C_8$-$C_{18}$-alkyl group bound to the nitrogen atom to the amphiphile (A).

In a fifth aspect, the instant invention provides the use of a cationic surfactant (B) which is selected from quaternary benzyl ammonium salts having a benzyl group and at least one $C_8$-$C_{18}$-alkyl group bound to the nitrogen atom for improving the hydrate inhibitor performance of an amphiphile (A) having the general formula (1) above.

In a sixth aspect, the instant invention provides a mixture of hydrocarbons and water comprising the composition of the first aspect of the invention, wherein the mixture has a reduced tendency to form hydrocarbon hydrate agglomerates under hydrate forming conditions.

Besides amphiphile (A) and cationic surfactant (B), the gas hydrate inhibitor composition according to the invention may optionally contain up to 30 wt.-% of a further surfactant (C) which is different from A) and B).

The term hydrate inhibitor performance includes the gas hydrate composition's capability to provide for enhanced anti-agglomeration and/or enhanced inhibition, retardation, mitigation, reduction, control, delay, and/or the like of agglomeration of hydrates and/or hydrate-forming compounds. In certain embodiments, agglomeration of hydrates and/or hydrate-forming compounds (and the like) may be reduced and/or inhibited to a greater degree than that achieved using the hydrate inhibitor components individually.

Synergistically improved hydrate inhibition means that the hydrate inhibitor performance of the combination of components A and B is greater than the sum of the action of each of the components when used alone. This means that either the hydrate inhibitor performance obtained with the combination of the compounds (A) and (B) is greater than expected from the sum of the individual components when used alone; or, alternatively, a predetermined hydrate inhibitor performance is achieved with a lower dose rate of the combination of components (A) and (B) than with each of the individual components when used alone. Whether or not there is a synergy between components A) and B) is determined by the reduced dose rate required to prevent gas hydrate agglomeration over the dose rate required of each of the individual components. Often the reduction of dosage rate is between 5 and 70 wt.-%, preferably between 10 and 40 wt.-% and most preferably between 20 and 35 wt.-% as for example between 5 and 40 wt.-%, or between 5 and 35 wt.-%, or between 10 and 50 wt.-%, or between 10 and 35 wt.-%, or between 20 and 70 wt.-%, or between 20 and 40 wt.-%. Alternatively, or in addition to the above, a synergistic effect between components A) and B) can be determined by comparison of secondary properties such as emulsion tendency, and more specifically of the water drop properties of the co-produced mixture of oil and water. The combination of components A) and B) results in a faster and more complete separation of water than obtained when one of the components is used alone.

The terms "hydrate" and "gas hydrate" are used interchangeably and refer to a gaseous mixture in a water clathrate; i.e. they refer to a solid hydrogen-bonded network of water molecules encapsulating gas molecules to form a cage-like structure or hydrate which is also known as clathrate. Especially, the terms refer to hydrates formed by low molecular weight hydrocarbons. Similarly, the terms "hydrate inhibitor" and "gas hydrate inhibitor" are used interchangeably, referring to additives inhibiting, retarding, mitigating, reducing, controlling and/or delaying formation of hydrates and/or agglomerates of hydrates and/or plugs.

Amphiphile (A)

Component (A) of the hydrate inhibitor composition according to the invention contains an amphiphile having the general formula (1) wherein a lipophilic tail $R^5$ which is a hydrocarbyl group having 6 to 22 carbon atoms is linked by a linking moiety L to a hydrophilic head group which comprises a N,N-dialkylamino group —$N(R^1)(R^2)$ wherein $R^1$ and $R^2$ are $C_1$-$C_5$-alkyl groups, or together with the nitrogen atom to which they are attached form a substituted or unsubstituted heterocyclic group, and wherein the N,N-dialkylamino group may be in the form of an ammonium compound. As used herein, the term "linking moiety" refers to any portion of the hydrate inhibitor component (A) that provides spacing between the lipophilic tail $R^5$ and the hydrophilic head group —$[N(R^1)(R^2)(R^3)]^+X^-$.

Preferably, the lipophilic tail $R^5$ of the amphiphile (A) is an alkyl or alkenyl group having 6 to 22 carbon atoms and especially preferred having 8 to 20 carbon atoms, as for example 6 to 18 carbon atoms, or 8 to 22 carbon atoms. Preferred alkyl and alkenyl groups may be linear, branched or cyclic and/or any combination thereof. Preferred alkyl and alkenyl residues $R^5$ are octyl, nonyl, decyl, undecyl, dodecyl, tridecyl, tetradecyl, hexadecyl, octadecyl, eicosyl, dodecenyl, tetradecenyl, hexadecenyl, octadecenyl, eicosenyl, and their mixtures. The alkyl- and alkenyl groups $R^5$ may be of natural or synthetic origin. In certain embodiments, the amphiphile may comprise one or more further lipophilic tails, for example alkyl or alkenyl residues stemming from substituents of the linking moiety L.

Preferred substituents $R^1$ and $R^2$ are alkyl residues having from 3 to 5 carbon atoms and especially preferred are those having 4 carbon atoms. The alkyl residues $R^1$ and $R^2$ may be linear, or when they have at least three carbon atoms they may be branched. Preferably they are linear. Examples for alkyl residues $R^1$ and $R^2$ are methyl, ethyl, n-propyl, iso-propyl, n-butyl, iso-butyl, tert-butyl, n-pentyl and iso-pentyl.

Preferred among those are n-propyl, iso-propyl, n-butyl, iso-butyl, tert-butyl, n-pentyl and iso-pentyl. Particularly preferred are n-butyl, iso-butyl, tert-butyl. The alkyl residues $R^1$ and $R^2$ may be the same or they may be different. Preferably, they are the same. In an especially preferred embodiment, the polar head group is a N,N-dibutylamino group.

The nitrogen atom, together with $R^1$ and $R^2$, may form a cycle. When the nitrogen atom, together with $R^1$ and $R^2$ forms a substituted or unsubstituted heterocyclic group, the group can be considered a "nitrogen-containing heterocycle". The nitrogen-containing heterocycle can denote optionally substituted, fully saturated or unsaturated, monocyclic or bicyclic, aromatic or nonaromatic groups having at least one nitrogen atom in at least one ring, and preferably 5 or 6 atoms in each ring. The nitrogen-containing heterocycle can also contain 1 or 2 oxygen atoms or 1 or 2 sulfur atoms in the ring. Exemplary nitrogen-containing heterocycles include pyrrole, pyrroline, pyrrolidine, piperidine, pyrazole, pyrazoline, pyrazolidine, imidazole, imidazoline, imidazolidine, triazole, isoxazole, isoxazoline, isoxazolidine, oxazole, oxazoline, oxazolidine, thiazole, isothiazole, oxadiazole, oxatriazole, dioxazole, oxathiazole, pyridine, pyridazine, pyrimidine, pyrazine, piperazine, triazine, oxazine, oxathiazine, oxazine, isoxazine, oxadiazine, morpholine, azepane, azepine, caprolactam, or quinoline. When substituted, exemplary substituents include one or more of the following groups: $C_1$-$C_{20}$alkyl, $C_2$-$C_{20}$ alkenyl, aryl, aralkyl, hydroxy, acyl, acyloxy, alkoxy, alkenoxy, aryloxy, halogen, amino, nitro, cyano, esters and ethers.

In a first preferred embodiment, the polar head group of the amphiphile (A) according to formula (1) is a tertiary amino group having, besides the bond to the linking moiety, substituents $R^1$ and $R^2$ while $R^3$ and $X^-$ are absent. In this embodiment amphiphile (A) is an amine of formula (1a)

    (1a)

wherein L, $R^1$, $R^2$ and $R^5$ have the meanings given above.

In a second preferred embodiment, the polar head group of the amphiphile (A) according to formula (1) is an ammonium compound wherein $R^3$ and $X^-$ are present. In this embodiment, amphiphile (A) is an ammonium compound of formula (1b)

    (1b)

wherein

L, $R^1$, $R^2$ and $R^5$ have the meanings given above;

$R^3$ is hydrogen or an alkyl group having from 1 to 8 carbon atoms which optionally bears a hydroxy group or a carboxy group in the 2-position; and $X^-$ is an anion.

In a preferred embodiment, $R^3$ is hydrogen. Such ammonium salt can be obtained by reaction of the above described tertiary amino group —$N(R^1)(R^2)$ of formula (1 a) with an acid. The acid may be organic or inorganic. Preferred inorganic acids are halide acids like HCl, HBr and HI; sulfuric acid, phosphoric acid, phosphorous acid, nitric acid, or a combination thereof. Preferred organic acids are carboxylic acids, sulfonic acids and phosphonic acids, as for example formic acid, acetic acid, propionic acid, butyric acid, acrylic acid, methacrylic acid, glycolic acid, pivalic acid, malic acid, maleic acid, succinic acid, thioglycolic acid, methane sulfonic acid, p-toluene sulfonic acid, the like, and any combination thereof.

Preferably, $X^-$ is selected from hydroxide, carboxylate, halide, sulphate, nitrite, nitrate, organic sulfonate, phosphate, organic phosphonate, and combinations thereof. Suitable halide ions include, without limitation, fluoride, chloride, bromide, iodide, and combinations thereof. Suitable carboxylates include anions stemming from carboxylic acids having from 1 to 20 carbon atoms, more preferably having from 2 to 12 carbon atoms and especially preferred having from 3 to 6 carbon atoms as for example having from 1 to 12, or from 1 to 6, or from 2 to 20, or from 2 to 6, or from 3 to 20, or from 3 to 12 carbon atoms. In a preferred embodiment, the carboxylic acid is aliphatic. Preferred aliphatic carboxylic acids may be linear or branched; they may be saturated or unsaturated. Examples for especially preferred carboxylates are formate, acetate, propionate, butyrate, pentanoate, hexanoate, acrylate, methacrylate, glycolate, malonate, succinate, trifluoroacetate, and mixtures thereof. Especially preferred the anion $X^-$ is selected from carboxylate, halide, acrylate, methacrylate, and combinations thereof; most preferred $X^-$ is acrylate. In an especially preferred embodiment, $X^-$ is the anion of the acid used for protonation of the amino group.

In a further preferred embodiment, $R^3$ is an alkyl group having from 1 to 8 carbon atoms. In some embodiments, when $R^3$ has 2 or more carbon atoms, $R^3$ may be substituted by a hydroxy group or with a carboxyl group in the 2-position of the alkyl group. Such quaternary ammonium compound wherein $R^3$ is an alkyl group can be obtained by reaction of the above described tertiary amino group —$N(R^1)(R^2)$ of formula (1 a) with an alkylating agent. The quaternizing agent may include alkyl halides, alkyl sulfates, oxalates, carbonates, hydrocarbyl epoxides and mixtures thereof. In some embodiments, the quaternizing agent may be a sulfate, such as dimethyl sulfate. In some embodiments, the quaternizing agent may be a halide, such as $CH_3Cl$. In some embodiments, the quaternizing agent may be a carbonate, such as dimethyl carbonate. In some embodiments, the quaternizing agent may be an epoxide, such as a hydrocarbyl epoxide, such as, for example, ethylene oxide, propylene oxide, butylene oxide, and the like. In some embodiments, the quaternizing agent may be acrylic acid or methacrylic acid. Especially preferred alkylating agents include methyl chloride, methyl bromide, methyl iodide, ethyl chloride, ethyl bromide, ethyl iodide, dimethyl sulfate, diethyl sulfate and any combination thereof. In a preferred embodiment, $X^-$ is the anion formed during reaction of the alkylating agent with the amino group as for example chloride, bromide, iodide, methosulfate, ethosulfate, the like and any combination thereof. In an especially preferred embodiment, $R^3$ is a methyl group.

The linking moiety L is defined as the part of the amphiphile (A) according to formula (1) which connects the hydrophilic head group —$N(R^1)(R^2)$, respectively —$[N(R^1)(R^2)(R^3)]^+X^-$, with the lipophilic tail $R^5$. The linking moiety L contains a connecting chain which constitutes the direct connection between the hydrophilic head group —$N(R^1)(R^2)$, respectively —$[N(R^1)(R^2)(R^3)]^+X^-$, and the lipophilic tail $R^5$ and which may have substituents attached to it. The connecting chain is made from carbon atoms, at least one heteroatom selected from oxygen and nitrogen and optionally one or more further heteroatoms. The atoms forming the connecting chain will be referred to as linking elements in the following. For the sake of clarity, the connecting chain does not include any substituents. In case the linking moiety L is a hydrocarbyl group having at least 2 adjacent carbon atoms, at least one heteroatom selected from nitrogen and oxygen, optionally one or more further heteroatoms and does not contain any substituents, the linking moiety L and the connecting chain are the same.

The linking moiety L may instead or in addition be characterized as an optionally substituted heteroaliphatic chain. Heteroaliphatic chain means that the link between lipophilic tail $R^5$ and hydrophilic head group —N($R^1$)($R^2$), respectively —[N($R^1$)($R^2$)($R^3$)]$^+$X$^-$ comprises a linear or branched chain made from carbon atoms which is interrupted by at least one heteroatom selected from oxygen and nitrogen and optionally one or more further heteroatoms selected from nitrogen, oxygen, phosphorous, and sulfur. In a preferred embodiment, at least one of the one or more further heteroatoms interrupting the optionally substituted heteroaliphatic chain is a nitrogen or an oxygen atom.

The linking moiety L may have heteroatoms attached to one or more of its carbon linking elements, but not more than one heteroatom per carbon linking element. Preferably, heteroatoms attached to the connecting chain are part of a functional group as for example a hydroxy, a carbonyl or a carboxymethyl group. Furthermore, alkyl groups and especially alkyl groups having 1 to 6 carbon atoms may be attached to carbon and/or nitrogen atoms of the connecting chain.

In a preferred embodiment, the connecting chain contains from 4 to 20, more preferably 5 to 14 and especially preferred 6 to 10 linking elements, as for example from 4 to 14, or from 4 to 12, or from 5 to 20, or from 5 to 12, or from 6 to 20, or from 6 to 14 linking elements. In a further preferred embodiment, the linking moiety L has a total of from 5 to 100, more preferably from 6 to 50, and especially preferred of from 6 to 20 atoms (carbon and hetero atoms, but excluding hydrogens), as for example from 5 to 50, or from 5 to 20, or from 6 to 100 atoms. For counting the number of atoms in the linking moiety and likewise in the connecting chain it is necessary to define the boundary between $R^5$ and the linking moiety L. Starting from the lipophilic tail $R^5$ which is a hydrocarbyl group not containing heteroatoms, the linking moiety begins at the position where there is either the first heteroatom or a carbon atom that is substituted with a group comprising at least one heteroatom.

In some embodiments, the nitrogen atom being part of the linking moiety is part of an amino, a polyamino, an ammonium, or a polyammonium, an amide and/or an imide group. The further heteroatom or heteroatoms which may be part of the connecting chain may be part of an ether, a polyether, an amino, a polyamino, an ammonium, or a polyammonium group. In further embodiments, such further heteroatom(s) may be part of a functional group as for example an ester, an amide and/or an imide group. In such embodiments the carbon atom of the carbonyl group and the heteroatom within the connecting chain both constitute members of the heteroaliphatic chain. In an especially preferred embodiment, the linking moiety contains at least one further nitrogen atom in the form of an amine or amide group.

In some embodiments, one or more heteroatoms may be attached to the connecting chain as a substituent as for example a hydroxy group, an amino group, a carboxylic acid group or a carboxylate group.

The connecting chain may instead or in addition be characterized as a heteroaliphatic chain which can be saturated or unsaturated, wherein one or more non-adjacent $CH_2$ groups are replaced by a heteroatom selected from nitrogen, oxygen, sulfur and phosphorous. The heteroatom may be part of a functional group. Preferred functional groups are selected from —C(=O)—O—, —O—C(=O)—, —C(=O)—N($R^6$)—, —N($R^7$)—C(=O), —N($R^6$)—, —($R^7$)N—, —O—, —S—, —(SO)— or —(SO$_2$)—, wherein $R^6$ is hydrogen or an alkyl group having from 1 to 5 carbon atoms, more preferably having 3 to 5 carbon atoms and especially preferred having 4 carbon atoms and wherein amino groups may be in form of their ammonium compound, and $R^7$ is hydrogen or an organic moiety having from 1 to 20 carbon atoms. Especially preferred $R^7$ is an alkyl group having from 1 to 20 carbon atoms.

Accordingly, the connecting chain may comprise one or more aliphatic groups having 2 to 10, preferably 3 to 6 and especially preferred 2 to 4 adjacent carbon atoms, which are connected to each other and/or the hydrophobic tail by a heteroatom or a functional group comprising a heteroatom whereby at least one heteroatom is a nitrogen or oxygen atom. Examples for preferred functional groups are —C(=O)—O—, —O—C(=O)—, —C(=O)—N($R^6$)—, —N($R^7$)—C(=O)—, —N($R^6$)—, —($R^7$)N—, —O—, —S—, —(SO)— and —(SO$_2$)—, wherein $R^6$ and $R^7$ have the meanings given above. Preferred aliphatic groups are alkylene groups as for example any one or more of ethylene, propylene, butylene, pentylene, hexylene, heptylene, octylene, nonylene, decylene. In an especially preferred embodiment, the linking moiety comprises one or more hydrocarbyl segments each having 2 to 4 carbon atoms wherein the segments are linked by a heteroatom selected from O and N or by a functional group comprising at least one of those heteroatoms. Preferred functional groups are esters and amides with amides being especially preferred.

In some preferred embodiments, the lipophilic tail $R^5$ may be connected to the hydrophilic head group —N($R^1$)($R^2$), respectively —[N($R^1$)($R^2$)($R^3$)]$^+$X$^-$ via a linking moiety L selected from the chemical structures (2) to (7):

  (2)

  (3)

  (4)

  (5)

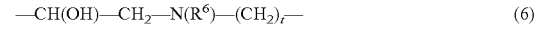  (6)

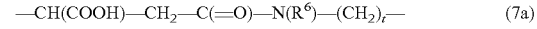  (7a)

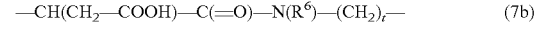  (7b)

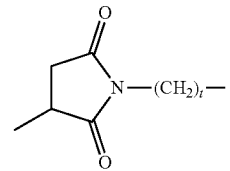  (7c)

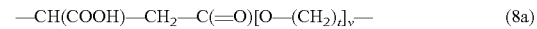  (8a)

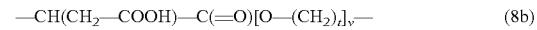  (8b)

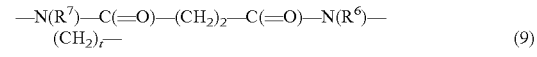  (9)

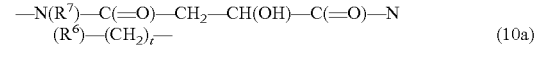  (10a)

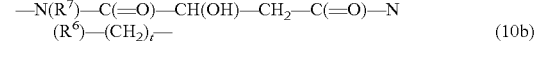  (10b)

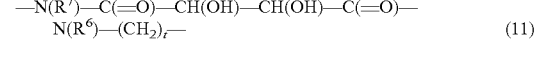  (11)

—N($R^7$)—C(=O)—C(OH)(CH$_2$COOH)—CH$_2$—C(=O)—N($R^6$)—(CH$_2$)$_t$— (12a)

—N($R^7$)—C(=O)—CH$_2$—C(OH)(CH(COOH))—C(=O)—N($R^6$)—(CH$_2$)$_t$— (12b)

wherein t is 2, 3 or 4;

v is an integer between 1 and 30 and preferably between 1 and 10;

$R^6$ is hydrogen or an alkyl group having from 1 to 5 carbon atoms, more preferably having 2 to 4 carbon atoms and especially preferred having 4 carbon atoms;

$R^7$ is hydrogen or an organic moiety having from 1 to 20 carbon atoms and more preferred hydrogen or an alkyl group having from 1 to 20 carbon atoms; and wherein amino groups may be in form of their ammonium compound.

In a preferred embodiment of the instant invention, the amphiphile (A) is an amido amine according to the general formula (13)

$$\left[ R^5 - \underset{R^8}{\overset{R^7}{N}} - [CH_2]_m - \overset{O}{C} - [CH_2]_o - \underset{R^6}{\overset{R^9}{N}} - R^4 \Big]_p \overset{R^1}{\underset{R^3}{N}} - R^2 \right]^{q+} [X^-]_q \qquad (13)$$

wherein $R^1$, $R^2$, $R^3$, $R^5$ and $X^-$ have the general meanings given above for formula (1) and its preferred embodiments;

$R^4$ is selected from —(CH$_2$)$_t$—, —[(CH$_2$—CHR$^{10}$)$_s$]—, —(CH$_2$—CHR$^{10}$O)$_u$—(CH$_2$)$_t$— and combinations thereof;

$R^6$ is hydrogen or an alkyl group having from 1 to 5 carbon atoms, more preferably having 1 to 4 carbon atoms and especially preferred being hydrogen, a methyl or a butyl group;

$R^7$ is hydrogen or an organic moiety having from 1 to 20 carbon atoms and more preferred hydrogen or an alkyl group having from 1 to 20 carbon atoms;

$R^8$ is present or not as hydrogen or an alkyl group having from 1 to 5 carbon atoms, more preferably having 1 to 4 carbon atoms and especially preferred being a methyl or butyl group, with the proviso that when m=0, $R^8$ is not present;

$R^9$ is present or not as hydrogen or an alkyl group having from 1 to 5 carbon atoms, more preferably having 1 to 4 carbon atoms and especially preferred being a methyl or butyl group, with the proviso that when o=0, $R^9$ is not present;

$R^{10}$ is an alkyl group having 1 to 4 carbon atoms;

s is 1, 2 or 3;

t is 2, 3 or 4;

u is an integer between 1 and 10 and preferably between 1 and 5;

n is 0 or 1 m is 0 or 2 o is 0 or 2 p is 0 or an integer between 1 and 5;

n+p is an integer between 1 and 6 and preferably 1; and q is 0 or an integer between 1 and 7, but not more than the sum of n+p+1.

In a preferred embodiment, the sum of m+o in formula 13 is 2. In a further preferred embodiment, m, n and o in formula 13 all are 0.

The number of anions q depends on the presence of $R^3$, Fe and/or $R^9$. For example, when $R^3$, $R^8$ and $R^9$ are not present, q is 0; when only one of $R^3$, Fe and $R^9$ is present, q is 1; when o is 2, m is 0 and $R^3$ as well as $R^9$ in all units —N($R^6$)($R^9$)—$R^4$— are present, q may be equal to p+1, i.e. it is an integer between 2 to 6, depending on the value of p.

In an especially preferred embodiment, the amphiphile (A) is an amido amine according to the general formula (14)

$$\left[ R^5 - \overset{O}{C} - \underset{R^6}{\overset{}{N}} - R^4 \Big]_p \overset{R^1}{\underset{R^3}{N}} - R^2 \right]^{q+} (X^-)_q \qquad (14)$$

wherein $R^1$, $R^2$, $R^3$, $R^5$ and $X^-$ have the general meanings given above;

$R^4$ is selected from —(CH$_2$)$_t$— and —[(CH$_2$—CHR$^{10}$)$_s$]— and more preferably is —(CH$_2$)$_t$—;

$R^6$ is hydrogen or an alkyl group having from 1 to 5 carbon atoms and more preferably is hydrogen;

$R^{10}$ is an alkyl group having from 1 to 4 carbon atoms;

p is an integer between 1 and 5;

s is 1, 2 or 3;

t is 2, 3 or 4 and most preferred t is 3;

q is 0 when $R^3$ is absent, or q is 1 when $R^3$ is present.

The embodiment of formula (14) can be derived from formula (13) wherein m, n and o are all 0.

In a preferred embodiment, p in formula (9) is 1 or 2, and especially preferred p is 1. In a further preferred embodiment, $R^3$ is hydrogen, and the anion $X^-$ is selected from hydroxide, carboxylate, halide, sulphate, organic sulfonate, and combinations thereof.

In some embodiments, the compound according to formula (14) is the reaction product of an N,N-dialkylaminoalkylamine of formula HN($R^6$)—$R^4$—N($R^1$)($R^2$) with a fatty acid of formula $R^5$—COOH, an ester of a fatty acid of formula $R^5$—COOH with an alcohol having 1 to 4 carbon atoms, or a fatty acid glyceride. Preferably, the fatty acid, fatty acid ester or fatty acid glyceride is derived from a plant source or an animal source selected from vegetable oils, as for example coconut oil, or tallow oil and combinations thereof.

In another embodiment, the compound according to formula (14) includes a product prepared by the reaction of an amine selected from 3-(dialkylamino)propylamine and 2-(dialkylamino)ethylamine with vegetable oil or tallow oil followed by neutralization with an acid or by quaternization with an alkylating agent. Preferred acids are selected from mineral acids and organic acids having from 1 to 20 carbon atoms, as for example formic acid, acetic acid, chloroacetic acid, propionic acid, acrylic acid, and methacrylic acid. Preferred alkylating agents are selected from an organic halide, such as an alkyl halide, having from 1 to 8 carbon atoms, dimethyl sulfate and C$_2$-C$_4$ alkylene oxides. Preferably, the dialkylamino group of the N,N-dialkylaminoalkylamine includes two alkyl groups independently selected from methyl, ethyl, propyl or butyl, and combinations thereof; or when $R^1$ and $R^2$ together with the nitrogen atom to which they are attached form a substituted or unsubstituted heterocyclic group having 5 or 6 atoms in the ring. Examples for preferred N,N-dialkylaminoalkylamines are N,N-dimethylaminoethylamine, N,N-dimethylaminopropylamine, N,N-diethylaminoethylamine, N,N-diethylaminopropylamine, N,N-dipropylaminoethylamine, N,N-dipropylaminopropylamine, N,N-dibutylaminoethylamine, N,N-dibutylaminopropylamine, N,N-dimethylaminopropylenediamine, N,N-dipropylaminopropylenediamine, N,N-dibutylaminopropylenediamine, N-(3-aminopropyl)pyrrolidine, N-(3-aminopropyl)piperidine, and N-(3-aminopropyl)azepane.

In further especially preferred embodiments, the amphiphile (A) is an amido amine according to one or more of formulae (15), (16) and/or (17):

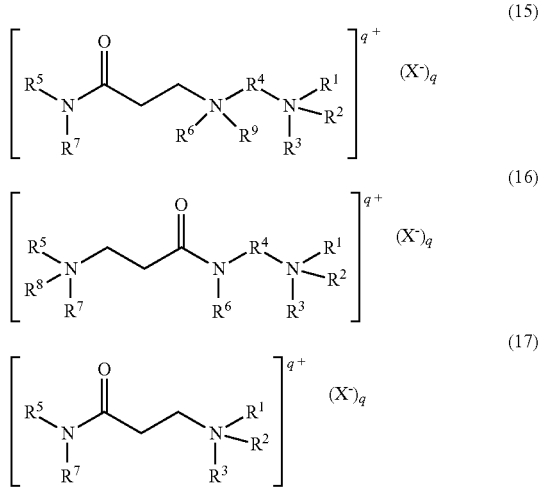

wherein
$R^1$, $R^2$, $R^3$, $R^5$ and $X^-$ have the meanings given above for formula (1);
$R^4$ is —$(CH_2)_t$—;
$R^6$ is hydrogen or an alkyl group having from 1 to 5 carbon atoms, more preferably having 2 to 4 carbon atoms and especially preferred being hydrogen, a methyl or a butyl group;
$R^7$ is hydrogen or an organic moiety having 1 to 20 carbon atoms and more preferred hydrogen or an alkyl group having from 1 to 20 carbon atoms;
$R^8$ and $R^9$ independently are present or not as hydrogen or an alkyl group having from 1 to 5 carbon atoms, more preferably having 2 to 4 carbon atoms and especially preferred being hydrogen, a methyl or a butyl group.
q is 0 when $R^3$, $R^8$ and $R^9$ are absent; and q is 1, 2 or 3 depending on the presence of one or more of $R^3$, $R^8$ and $R^9$; and
t is 2, 3 or 4 and most preferred t is 3.

For instance, in some embodiments, the amphiphile (A) according to formula (16) may be characterized as the reaction product of (i) a N,N-dialkylaminoalkylamine having the general formula $HN(R^6)$—$R^4$—$N(R^1)(R^2)$ and (ii) a first intermediate formed as the reaction product of one or more ethylenically unsaturated carboxylic acids or esters and an alkyl amine $HN(R^5)(R^7)$. The ethylenically unsaturated carboxylic acids or esters may be an alkyl alkenoate (e.g., an alkyl methacrylate, an alkyl acrylate (for example, methyl acrylate)), an alkenoic acid (e.g., acrylic acid), and any combination thereof. For example, cocoylamine or oleylamine can first be reacted with methyl acrylate and the reaction product can be further reacted with a N,N-dialkylaminoalkylamine as for example N,N-dimethylaminopropylamine, N,N-dibutylaminopropylamine, pyrrolidine or the like to form an amide.

In some embodiments, the amphiphile (A) according to formulae (15) and (17) may be characterized as the reaction product of: (i) an alkyl amine having the formula —$N(R^5)(R^7)$ and ii) a first intermediate formed as the reaction product of one or more ethylenically unsaturated carboxylic acids or esters (e.g., acrylates, methacrylates (for example, methyl acrylate)) and a N,N-dialkylamine having the general formula $H[N(R^6)$—$R^4]_p$—$N(R^1)(R^2)$. For example, a secondary amine wherein p=0 having the formula $HN(R^1)(R^2)$ as for example dimethylamine, dibutylamine, or a N,N-dialkylaminoalkylamine wherein p=1 having the formula $HN(R^6)$—$R^4$—$N(R^1)(R^2)$ as for example N,N-dimethylaminopropylamine, N,N-dibutylaminopropylamine, pyrrolidine or the like can be reacted with methyl acrylate. The so formed intermediate reaction product can then be reacted with an alkyl amine having the formula —$N(R^5)(R^7)$ as for example cocoylamine or oleylamine to form an amide.

Via both of the reaction pathways leading to amphiphiles (A) according to formulae (15), (16) and (17), the lipophilic tail(s) $R^5$ and optionally $R^7$ are introduced into the amphiphile (A) by the choice of the alkyl amine according to formula $HN(R^5)(R^7)$. Preferred alkyl amines $HN(R^5)(R^7)$ for reaction with the ethylenically unsaturated carboxylic acid or ester respectively with the first intermediate formed from the ethylenically unsaturated acid or ester with the N,N-dialkylamine may include, but are not limited to, any primary or secondary fatty amine derived from one or more fatty acids having 6 to 22 carbon atoms or its esters. Preferably the alkyl amine $HN(R^5)(R^7)$ is derived from a fatty acid or ester selected from the group consisting of: corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and any combination thereof. Suitable alkyl amines for reaction also may include, but are not limited to, any synthetic primary or secondary amine including, but not limited to, hexylamine, octylamine, dodecylamine, tridecylamine, tetradecylamine, N-methyldodecylamine, N-methyloctylamine, didodecylamine, and the like, and any combination thereof.

In some embodiments, the reaction product of the N,N-dialkylaminoalkylamine $H[N(R^6)$—$R^4]_p$—$N(R^1)(R^2)$, the unsaturated carboxylic acid and the alkyl amine $HN(R^5)(R^7)$ in either sequence may form a second intermediate that may further be reacted with (iii) one or more acids, or with one or more alkylating agents to form the hydrate inhibitor. In such embodiments, $R^3$ and/or $R^8$ of the cation moiety may depend upon, among other factors, the alkyl group of the alkylating agent(s). In certain embodiments, the one or more acids of formula HX may be an inorganic acid as for example a halide acid, or a carboxylic acid, as for example formic acid, acetic acid propionic acid, acrylic acid, methacrylic acid or the like. In certain embodiments, the one or more alkylating agents may be a carbonate, a halide, a sulfate, an organic sulfonate, a hydroxide, and/or any combination thereof.

In further especially preferred embodiments, the linking moiety L of amphiphile (A) may comprise a structure of formula (6). Such hydrate inhibitor compounds may be characterized as a reaction product of a N,N-dialkylaminoalkylamine of formula $HN(R^6)-R^4-N(R^1)(R^2)$ wherein $R^1$, $R^2$, $R^4$ and $R^6$ have the same meanings as given above, and a 1,2-epoxyalkane of formula (18)

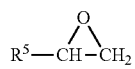 (18)

wherein $R^5$ has the meaning given above. Examples of preferred 1,2-epoxyalkanes are 1,2-epoxydecane, 1,2-epoxydodecane, 1,2-epoxytetradecane, 1,2-epoxyhexadecane 1,2-epoxyoctadecane and their mixtures. In some embodiments, the reaction product of the N,N-dialkylaminoalkylamine and the 1,2-epoxyalkane may further be reacted with one or more acids and/or alkylating agents whereby the same acids and alkylating agents are preferred as in the preceding embodiments.

In further especially preferred embodiments, the linking moiety L of amphiphile (A) may comprise one or more of structural elements (7a), (7b) and/or (7c). Such hydrate inhibitor compounds may be characterized as reaction products of a dicarboxylic acid reactant substituted with a hydrocarbyl substituent $R^5$ with a nitrogen containing compound having, besides a group $-N(R^1)(R^2)$, an oxygen or nitrogen atom capable of condensing with said dicarboxylic acid reactant.

Preferred dicarboxylic acid reactants substituted with a hydrocarbyl substituent $R^5$ are alkylsuccinic acids, alkenylsuccinic acids and their anhydrides. Preferably, the nitrogen compound is a N,N-dialkylaminoalkylamine having the structure $H-[N(R^6)-R^4]_p-N(R^1)(R^2)$ or a N,N-dialkylaminoalkanol having the structure $HO-R^4-N(R^1)(R^2)$, wherein $R^1$, $R^2$, $R^4$, $R^6$ and p have the same meanings as given above. The reaction product between a dicarboxylic acid reactant substituted with a hydrocarbyl substituent $R^5$ and a N,N-dialkylaminoalkylamine may be an amide according to formula (7a) or (7b), or an imide according to formula (7c). The reaction product between a dicarboxylic acid reactant substituted with a hydrocarbyl substituent $R^5$ and a N,N-dialkylaminoalkanol may be an ester according to formula (8a) or (8b) and will be similarly suited as amphiphile (A). In some embodiments, the reaction product of the dicarboxylic acid reactant with the nitrogen containing compound may further be reacted with one or more acids and/or quaternizing agents suitable for converting the amino group $-N(R^1)(R^2)$ to a quaternary nitrogen compound $-N(R^1)(R^2)(R^3)^+X^-$ whereby the same acids and alkylating agents are preferred as in the preceding embodiments.

In a further especially preferred embodiment, the linking moiety L of amphiphile (A) comprises a structure of formulae (9), (10a), (10b), (11), (12a) and (12b). Such hydrate inhibitor compounds may be characterized as unsymmetrically substituted dicarboxylic acid diamido ammonium compounds. They may be obtained by sequentially condensing a dicarboxylic acid with a fatty amine $HN(R^5)(R^7)$ to give an intermediate amide and/or imide, followed by the reaction of the intermediate amide and/or imide with a N,N-dialkylaminoalkylamine having the structure $H-[N(R^6)-R^4]_p-N(R^1)(R^2)$. The reversed sequence of reaction steps will result in a similar product. Preferred dicarboxylic acids have 4 to 14 and especially preferred 2 to 8 carbon atoms. The dicarboxylic acid may be further substituted by one or more hydroxy, carboxyl or carboxymethyl groups. Examples of preferred dicarboxylic acids are succinic acid (leading to formula (9)), malic acid leading to formulae (10a) and (10b)), tartaric acid leading to formula (11)) and citric acid (leading to formulae (12a) and (12b)). The thus obtained N,N-dialkylaminoalkylamide may be further reacted with an acid to form an ammonium salt or it may be quaternized with an alkylating agent whereby the same acids and alkylating agents are preferred as in the preceding embodiments.

The amphiphile (A) may be a single amphiphile or a mixture of two or more different amphiphiles. When (A) is a mixture of different amphiphiles, the components may differ in their chemical and/or physicochemical properties as for example in the alkyl chain length and/or the branching of the lipophilic tail $R^5$, the chain length of the alkyl residues $R^1$ and $R^2$ and/or the structure of the linking moiety L.

Cationic Surfactant (B)

In a preferred embodiment, the cationic surfactant (B) is a quaternary benzyl ammonium compound of the formula (19):

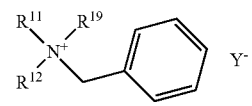 (19)

wherein
$R^{11}$ is an alkyl group having 8 to 18 carbon atoms,
$R^{12}$ is an alkyl group having from 1 to 5 carbon atoms,
$R^{19}$ is an alkyl group having from 1 to 18 carbon atoms, and
$Y^-$ is an anion.

In a preferred embodiment, $R^{11}$ is an alkyl group having from 8 to 16 and more preferred from 10 to 14 carbon atoms, as for example from 8 to 14, from 10 to 18, or from 10 to 16 carbon atoms. The alkyl group may be linear or branched. Preferably it is linear. Examples for preferred alkyl residues are octyl, iso-nonyl, decyl, iso-undecyl, dodecyl, iso-tridecyl, tetradecyl, pentadecyl, hexadecyl, octadecyl, and any mixtures thereof. In a preferred embodiment, $R^{11}$ comprises a mixture of different alkyl groups within the given chain lengths. These may be derived from renewable sources as for example coconut oil, sunflower oil, tallow fat, hardened tallow fat, ???

In a preferred embodiment, $R^{12}$ is an alkyl group having from 1 to 4 carbon atoms. The alkyl group may be linear or branched. More preferably, it is linear. Examples for preferred residues $R^{12}$ are methyl, ethyl, propyl, n-butyl, sec-butyl and tert-butyl. Especially preferred is the methyl group.

In a preferred embodiment, $R^{19}$ is an alkyl group having from 1 to 5 carbon atoms and more preferred from 1 to 4 carbon atoms. The alkyl group may be linear or branched. More preferably, it is linear. Examples for preferred residues $R^{19}$ are methyl, ethyl, propyl, n-butyl, sec-butyl and tert-butyl. Especially preferred is the methyl group. In this embodiment $R^{19}$ may be the same as $R^{12}$ or it may be different. In an especially preferred embodiment $R^{12}$ and $R^{19}$ both are methyl groups.

In a further preferred embodiment, $R^{19}$ has from 8 to 16 and more preferred from 10 to 14 carbon atoms, as for example from 8 to 14, from 10 to 18, or from 10 to 16 carbon atoms. In this embodiment, the preferred embodiments for $R^{19}$ are the same as for $R^{11}$. $R^{19}$ may be the same as $R^{11}$ or it may be different. In a preferred embodiment, $R^{11}$ and $R^{19}$ are the same.

Preferably, $Y^-$ is an anion selected from $Cl^-$, $Br^-$, $I^-$, $CH_3SO_4^-$ and $C_2H_5SO_4^-$.

Examples for preferred cationic surfactants (B) are octyl dimethyl benzyl ammonium chloride, nonyl dimethyl benzyl ammonium chloride, decyl dimethyl ammonium chloride, dodecyl dimethyl benzyl ammonium chloride, tridecyl dimethyl benzyl ammonium chloride, tetradecyl dimethyl benzyl ammonium chloride, pentadecyl dimethyl benzyl ammonium chloride, hexadecyl dimethyl benzyl ammonium chloride, octadecyl dimethyl benzyl ammonium chloride, decyl dibutyl ammonium chloride, dodecyl dibutyl benzyl ammonium chloride, tridecyl dibutyl benzyl ammonium chloride, tetradecyl dibutyl benzyl ammonium chloride, pentadecyl dibutyl benzyl ammonium chloride, hexadecyl dibutyl benzyl ammonium chloride, octadecyl dibutyl benzyl ammonium chloride, dioctyl methyl benzyl ammonium chloride, dinonyl methyl benzyl ammonium chloride, didecyl methyl ammonium chloride, didodecyl methyl benzyl ammonium chloride, ditridecyl methyl benzyl ammonium chloride, ditetradecyl methyl benzyl ammonium chloride, dihexadecyl methyl benzyl ammonium chloride, dioctadecyl methyl benzyl ammonium chloride, octyl butyl methyl benzyl ammonium chloride, nonyl butyl methyl benzyl ammonium chloride, decyl butyl methyl benzyl ammonium chloride, dodecyl butyl methyl benzyl ammonium chloride, tridecyl butyl methyl benzyl ammonium chloride, tetradecyl butyl methyl benzyl ammonium chloride, hexadecyl butyl methyl benzyl ammonium chloride, octadecyl butyl methyl benzyl ammonium chloride and the respective bromide, iodide and methosulfate salts, and any combinations thereof.

The quaternary benzyl ammonium compounds (B) and their methods of preparation are well known to the ones skilled in the art.

In the gas hydrate inhibitor composition according to the invention the portion of the cationic surfactant (B) is between 5 and 95 wt.-%, preferably between 10 and 85 wt.-% and especially preferred between 20 and 60 wt.-% based on the combined masses of (A) and (B), as for example between 5 and 85 wt.-%, or between 5 and 60 wt.-%, or between 10 and 95 wt.-%, or between 10 and 60 wt.-%, or between 20 and 95 wt.-%, or between 20 and 85 wt.-% of the combined masses of (A) and (B).

In another preferred embodiment, the portion of the amphiphile (A) in the gas hydrate inhibitor composition according to the invention is between 5 and 95 wt. %, preferably between 15 and 90 wt.-% and especially preferred between 40 and 80 wt.-%, as for example between 5 and 90 wt.-%, or between 5 and 80 wt.-%, or between 15 and 95 wt.-%, or between 15 and 80 wt.-%, or between 40 and 95 wt.-%, or between 40 and 90 wt.-% of the combined masses of (A) and (B).

In a further preferred embodiment, the weight ratio between amphiphile (A) and cationic surfactant (B) is between 20:1 and 1:20, more preferably between 1:10 and 10:1 and especially preferred between 1:3 and 3:1 as for example between 20:1 and 1:10, or between 20:1 and 1:3, or between 10:1 and 1:20, or between 10:1 and 1:3, or between 1:3 and 1:20, or between 1:3 and 1:10.

In a preferred embodiment, the combination of components (A) and (B) will provide a synergistic improvement of the performance of component (A) respectively component (B) when used individually. Accordingly, the invention in its fourth aspect provides a method for improving the hydrate inhibitor performance of an amphiphile (A), the method comprising the addition of a quaternary benzyl ammonium salt (B) to the amphiphile (A). According to its fifth aspect the invention provides the use of a cationic surfactant selected from quaternary benzyl ammonium salts (B) for improving the hydrate inhibitor performance of an amphiphile (A).

Further Surfactants (C)

Besides amphiphile (A) and cationic surfactant (B), the hydrate inhibitor composition may contain one or more further surfactants (C). Often the further surfactant (C) may further improve the hydrate inhibitor performance of the combination of amphiphile (A) and cationic surfactant (B). A surfactant as defined herein is a compound that will decrease the surface tension when added to the aqueous compositions as described herein. In a comparison of the aqueous composition with and without surfactant (C), the aqueous composition with surfactant needs to have a lower surface tension. Further surfactants (C) may be selected from anionic, nonionic, zwitterionic (amphoteric) and cationic surfactants, wherein the further cationic surfactant (C) is different from the amphiphile (A) and the cationic surfactant (B).

Surfactants for use in the present invention typically contain hydrophobic groups such as alkenyl, cycloalkenyl, alkyl, cycloalkyl, aryl, alkyl/aryl or more complex aryl moieties being from $C_8$ to $C_{22}$, preferably $C_{10}$ to $C_{20}$, typically $C_{12}$ to $C_{18}$, and a hydrophilic moiety which may be nonionic, anionic, cationic, or amphoteric. Further hydrophobic groups included in the invention are polysiloxane groups and polyoxypropylene groups.

Typically, the further cationic surfactant may be any water-soluble compound having a positively ionized group, usually comprising a nitrogen atom, and either one or two alkyl groups each having an average of from $C_8$ to $C_{22}$. The anionic portion of the further cationic surfactant may be any anion which confers water solubility, such as formate, acetate, lactate, tartrate, citrate, chloride, nitrate, sulfate or an alkyl sulfate ion having up to $C_4$ such as a higher alkyl sulfate or organic sulfonate.

In some embodiments, the further surfactant (C) is a cationic surfactant according to formula (20)

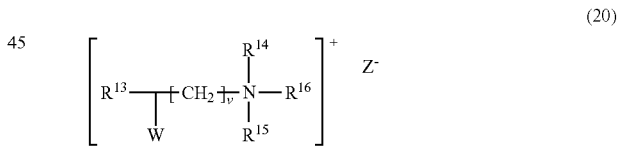

(20)

wherein $R^{13}$ is $C_8$ to $C_{22}$ alkyl or alkenyl;

$R^{14}$ an alkyl group having from 1 to 4 carbon atoms;

$R^{15}$ is hydrogen or an alkyl group having from 1 to 4 carbon atoms;

$R^{16}$ is hydrogen, an alkyl group having from 1 to 16 carbon atoms, or an aromatic hydrocarbon having from 6 to 16 carbon atoms, wherein 1 to 3 carbon atoms may be replaced by nitrogen and/or oxygen;

v is 0 or 1;

W H or OH;

$Z^-$ is an anion; and the further cationic surfactant (C) is different from cationic surfactant (B).

In some embodiments, the further cationic surfactant (C) comprises or consists of an N-alkyl pyridinium salt wherein the alkyl group has an average of from $C_8$ to $C_{22}$, preferably $C_{10}$ to $C_{20}$ carbon atoms. Other similarly alkylated heterocyclic salts, such as N-alkyl isoquinolinium salts, may also be used. Similarly, alkylammonium salts having one or at most two long aliphatic chains per molecule (e.g. chains having an average of $C_8$ to $C_{20}$ each, preferably $C_{12}$ to $C_{18}$ each) and two or three short chain alkyl groups having $C_1$ to $C_4$ each, e.g. methyl, ethyl, propyl and/or butyl groups, preferably methyl groups, may also be used as further cationic surfactant (C). Other classes of further cationic surfactants which are of use in the present invention include so called alkyl imidazoline or quaternized imidazoline salts having at least one alkyl group in the molecule with an average of from $C_8$ to $C_{22}$ preferably $C_{10}$ to $C_{20}$. Typical examples include alkyl methyl hydroxyethyl imidazolinium salts, alkyl benzyl hydroxyethyl imidazolinium salts, and 2 alkyl-1-alkylamidoethyl imidazoline salts. Alkyl phosphonium and hydroxyalkyl phosphonium salts having one $C_8$ to $C_{20}$ alkyl group and three $C_1$ to $C_4$ alkyl or hydroxyalkyl groups may also be used as further cationic surfactants (C) in the present invention.

In some embodiments, the further surfactant (C) is an anionic surfactant. The further anionic surfactant may for example comprise or consist of an at least sparingly water-soluble salt of sulfonic or mono-esterified sulfuric acids, e.g. an alkylbenzene sulfonate, alkyl sulfate, alkyl ether sulfate, olefin sulfonate, alkane sulfonate, alkylphenol sulfate, alkylphenol ether sulfate, alkylethanolamide sulfate, alkylethanolamidether sulfate, or alpha sulfo fatty acid or its ester each having at least one alkyl or alkenyl group with from 8 to 22, more usually from 10 to 20 aliphatic carbon atoms.

Other anionic surfactants useful as further surfactant (C) include alkyl sulfosuccinates, such as sodium dihexylsulfosuccinate, alkyl ether sulfosuccinates, alkyl sulfosuccinamates, alkyl ether sulfosuccinamates, acylsarcosinates, acyl taurides, isethionates, soaps such as stearates, palmitates, resinates, oleates, linoleates and alkyl ether carboxylates. Anionic phosphate esters and alkyl phosphonates, alkylamino and imino methylene phosphonates may equally be used.

In each case the anionic surfactant typically contains at least one alkyl or alkenyl chain having from 8 to 22, preferably from 10 to 20 carbon atoms. The expression "ether" here-in-before refers to compounds containing one or more glyceryl groups and/or oxyalkylene or polyoxyalkylene groups and especially a group containing from 1 to 150 oxyethylene and/or oxypropylene groups. One or more oxybutylene groups may additionally or alternatively be present. For example, the sulfonated or sulfated surfactant may be sodium dodecyl benzene sulfonate, potassium hexadecyl benzene sulfonate, sodium dodecyl, dimethyl benzene sulfonate, sodium lauryl sulfate, sodium tallow sulfate, potassium oleyl sulfate, ammonium lauryl sulfate, sodium tallow sulfate, potassium oleyl sulfate, ammonium lauryl monoethoxy sulfate, or monethanolamine cetyl 10 mole ethoxylate sulfate.

Preferred anionic surfactants are sodium salts. Other salts of commercial interest include those of potassium, lithium, calcium, magnesium, ammonium, monoethanolamine, diethanolamine, triethanolamine, alkyl amines containing up to seven aliphatic carbon atoms, and alkyl and/or hydroxyl alkyl phosphonium.

In some embodiments, the further surfactant (C) is a non-ionic surfactant. The non-ionic surfactant may be e.g. polyethoxylated alcohols, polyethoxylated mercaptans, glucamines and their alkoxylates, glucamides and their alkoxylates, alkylpolyglucacides, polyethoxylated carboxylic acids, polyethoxylated amines, polyethoxylated alkylolamides, polyethoxylated alkylphenols, polyethoxylated glyceryl esters, polyethoxylated sorbitan esters, polyethoxylated phosphate esters, polyethoxylated tertiary acetylenic glycols, and the propoxylate or ethoxylated and propoxylated analogues of all the aforesaid ethoxylated non-ionics, all having a $C_8$ to $C_{22}$ alkyl or alkenyl group and up to 20 ethyleneoxy and/or propyleneoxy groups. Also suited are partial esters of polyhydric compounds having three or more as for example three to six hydroxyl groups with fatty acids. In some embodiments the polyol may be glycerol, trimethylolpropane, erythritol, pentaerythrit, sorbitan, sorbitol, xylitol and their mixtures. Further included are polyoxypropylene/polyethylene oxide block copolymers, polyoxybutylene/polyoxyethylene copolymers and polyoxybuylene/polyoxypropylene copolymers. The polyethoxy, polyoxypropylene and polyoxybutylene compounds may be end capped with, e.g. methyl or benzyl groups to reduce the foaming tendency. Other non-ionic surfactants (C) which may optionally be present include $C_8$ to $C_{22}$ alkanolamides of a mono or di-lower alkanolamine, such as coconut monoethanolamide.

In some embodiments, the further surfactant (C) is an amphoteric surfactant. The amphoteric surfactant may for example be a betaine, e.g. a betaine of the formula $(R^{17})_3N^+CH_2COO^-$, wherein each $R^{17}$ may be the same or different and is an alkyl, cycloalkyl, alkenyl or alkaryl group and preferably at least one, and more preferably not more than one $R^{17}$ has an average of from $C_8$ to $C_{20}$, e.g. $C_{10}$ to $C_{18}$ of an aliphatic nature and each other $R^{17}$ has an average of from $C_1$ to $C_4$.

Other amphoteric surfactants suited for use as further surfactant (C) include quaternary imidazolines, alkyl amine ether sulfates, sulfobetaines and other quaternary amine or quaternised imidazoline sulfonic acids and their salts, and zwitterionic surfactants, e.g. N-alkyl taurines, carboxylates amidoamines such as $R^{18}CONH(CH_2)_2N^+(CH_2CH_2CH_3)_2$ $—CH_2CO^-_2$ and amido acids having, in each case, hydrocarbon groups capable of conferring surfactant properties ($R^{18}$ is either alkyl, cycloalkyl, alkenyl or alkaryl groups having from $C_8$ to $C_{20}$ of an aliphatic nature). Typical examples include 2-tallow alkyl, 1-tallow amido alkyl, 1-carboxymethyl imidazoline and 2-coconut alkyl N-carboxymethyl 2 (hydroxyalkyl) imidazoline. Generally speaking, any water soluble amphoteric or zwitterionic surfactant compound which comprises a hydrophobic portion including $C_8$ to $C_{20}$ alkyl or alkenyl group and a hydrophilic portion containing an amine or quaternary ammonium group and a carboxylate, sulfate or sulfonic acid group may be used in the present invention.

Similarly, suited amphoteric surfactants (C) are amine oxides e.g. amine oxides containing one or two (preferably one) $C_8$ to $C_{22}$ alkyl groups, the remaining substituent or substituents being preferably lower alkyl groups, e.g. $C_1$ to $C_4$ alkyl groups or benzyl groups. Particularly preferred for use as further surfactant (C) according to the current invention are surfactants which are effective as wetting agents; typically, such surfactants are effective at lowering the surface tension between water and a hydrophobic solid surface. Surfactants are preferred which do not stabilize foams to a substantial extent.

In a preferred embodiment, the further surfactant (C) includes at least one N-alkyl-N-acylglucamine according to formula (21)

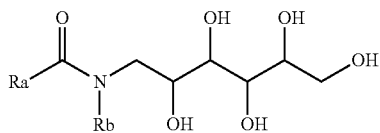

(21)

wherein

Ra is a linear or branched, saturated or unsaturated $C_5$-$C_{21}$-hydrocarbon residue, preferably a $C_7$-$C_{13}$-hydrocarbon residue, and Rb is a $C_1$-$C_4$ alkyl residue, preferably methyl.

In another preferred embodiment, the further surfactant (C) includes at least one cyclic N-Alkyl-N-acylglucamine selected from the formulae (22), (23), and/or (24)

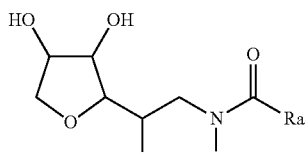

(22)

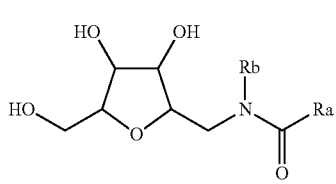

(23)

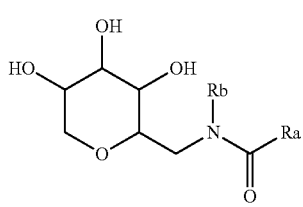

(24)

wherein Ra and Rb have the same meanings as given above

Polyfluorinated anionic, nonionic or cationic surfactants may also be present as further surfactant (C). Examples of such surfactants are polyfluorinated alkyl sulfates and polyfluorinated quaternary ammonium compounds.

Mixtures of two or more of the foregoing further surfactants (C) may be used. They may be of the same or different ionicity. In some embodiments, mixtures of non-ionic surfactants with cationic and/or amphoteric surfactants may be used. Typically, mixtures of anionic and cationic surfactants are avoided, which are often less mutually compatible.

In a preferred embodiment, the share of the further surfactant (C) in the gas hydrate inhibitor composition according to the invention is between 1 and 30 wt.-%, preferably between 3 and 20 wt.-% and especially preferred between 5 and 10 wt.-% based on the combined masses of (A) and (B), as for example between 1 and 20 wt.-%, or between 1 and 10 wt.-%, or between 3 and 30 wt.-%, or between 3 and 10 wt.-%, or between 5 and 30 wt.-%, or between 5 and 20 wt.-% of the combined masses of (A) and (B). This means that the further surfactant (C) is added on top into a composition comprising (A) and (B) in an amount that is up to 30% of the combined masses of (A) and (B). In an especially preferred embodiment, the gas hydrate inhibitor composition according to the invention does not contain a further surfactant.

The presence of the further surfactant (C) will provide a further improvement of the performance of components (A) and (B). For example, it will allow for further reduction of treat rates even beyond the two-component system comprising A and B only. Additionally, it may further improve upon secondary properties, which can further reduce the need for additional treatments to address undesirable secondary properties (i.e. emulsion breaker to address emulsion formation).

Application

In its second aspect, this invention relates to a method for inhibiting the agglomeration of hydrates and often also the formation of hydrates, wherein the composition according to the first aspect of the invention is brought into contact with a system comprising water and a gas and being susceptible to hydrate formation. The method may be applied to prevent or reduce or mitigate plugging of conduits, pipes, transfer lines, pipelines, valves, and other places or equipment where hydrocarbon hydrate solids may form under the conditions.

In its third aspect, this invention relates to the use of a composition according to the first aspect of the invention for inhibiting the agglomeration of hydrates and often also the formation of hydrates. The composition according to the first aspect of the invention may be used to prevent or reduce or mitigate plugging of conduits, pipes, transfer lines, pipelines, valves, and other places or equipment where hydrocarbon hydrate solids may form under the conditions.

The term "inhibiting" or "inhibited" is used herein in a broad and general sense to mean any improvement in preventing, reducing, retarding, mitigating, controlling and/or delaying the formation, growth and/or agglomeration of hydrates, especially of hydrocarbon hydrates and particularly of light hydrocarbon gas hydrates in any manner, including, but not limited to kinetically, thermodynamically, by dissolution, by breaking up, by dispersion, other mechanisms, or any combinations thereof.

The term "formation" or "forming" relating to hydrates is used herein in a broad and general manner to include, but not being limited to, any formation of hydrate solids from water and gases and especially from water and hydrocarbon(s) or hydrocarbon gas(es), growth of such hydrate solids, agglomeration of such hydrates, accumulation of hydrocarbon hydrates on surfaces, any deterioration of hydrate solids plugging or other problems in a system and combinations thereof.

The method according to the second aspect of the invention and the use of the hydrate inhibitor composition according to the third aspect of the invention are equally useful for inhibiting hydrate formation for many gases. They are especially useful for inhibiting hydrate formation of hydrocarbons, hydrocarbon gases and their mixtures. They are particularly useful for treatment of lighter and/or low-boiling, $C_1$ to $C_5$ hydrocarbon gases or gas mixtures at elevated pressure and/or low temperature conditions. Non-limiting examples of such "low-boiling" gases include methane, ethane, propane, n-butane, isobutane, isopentane and mixtures thereof as for example those encountered in natural gas including various natural gas mixtures that are present in many gas and/or oil formations and natural gas liquids (NGL). The hydrates of all these low-boiling hydrocarbons are also referred to as gas hydrates. In embodiments, the compositions and methods according to this invention are useful for inhibiting gas hydrate formation in a variety of black oils, heavy black oils to condensates, from API 10-60. The hydrocarbons and hydrocarbon gases may also comprise other compounds including, but not limited to hydrogen, carbon dioxide, hydrogen sulfide, and other compounds commonly found in gas/oil formations or processing plants, either naturally occurring or used in recovering/processing hydrocarbons from the formation or both, and mixtures thereof.

In embodiments, the gas hydrate inhibitor composition is applied to fluids that contain various levels of oil, brine or both having various levels of salinity. In one embodiment, the fluid has a salinity of about 0.1 to about 25 wt.-% or about 10 to about 25 wt.-%.

In some embodiments, the hydrate inhibitor composition is applied to a fluid that contains various levels of water cut. One of ordinary skill in the art understands that "water cut" refers to the volume percent of water in a composition containing an oil and water. In a preferred embodiment, the water cut is from about 1 to about 80 vol.-%. In more preferred embodiments, the water cut is from about 1 to about 60 vol.-%, from about 5 to about 40 vol.-%, from about 10 to about 30 vol.-% as for example from about 1 to 40 vol.-%, or from about 1 to 30 vol.-%, or from about 5 to 80 vol.-%, or from about 5 to 60 vol.-%, or from about 5 to 30 vol.-%, or from about 10 to 80 vol.-%, or from about 10 to 60 vol.-%, or from about 10 to 40 vol.-%, or from about 15 to about 80 vol.-% with respect to the total volume of water and hydrocarbon phases. The combination of the amphiphile (A) with the cationic surfactant (B) according to the invention allows to increase the maximum treatable water cut over the use of the individual components.

The method according to the second aspect and the use according to the third aspect of the present invention involve contacting a mixture of a gas and water and especially a mixture of hydrocarbon gas and water susceptible to hydrate formation with a composition according to the first aspect of the invention. When an effective amount of the composition is used, hydrate blockage is inhibited. In the absence of such effective amount, hydrate blockage is not inhibited.

The compounds of the present invention are added into the mixture of hydrocarbons and water at any concentration effective to inhibit the formation of hydrates under the given conditions. Preferably, the concentration of the active gas hydrate inhibitor composition added into the mixture of hydrocarbons and water is between 0.001 wt.-% and about 4.0 wt.-% relative to the total weight of the aqueous phase being part of the mixture of fluids, water and hydrocarbon, to be inhibited from hydrate formation. More preferably, the gas hydrate inhibitor composition concentration is between about 0.005 wt.-% and about 1.5 wt.-% and especially preferred between about 0.01 wt.-% and about 0.50 wt.-%, as for example between about 0.001 wt.-% and about 1.5 wt.-%, or between about 0.001 wt.-% and about 0.5 wt.-%, or between about 0.005 wt.-% and about 4.0 wt.-%, or between about 0.005 wt.-% and about 0.5 wt.-%, or between about 0.01 wt.-% and about 4.0 wt.-%, or between 0.01 wt.-% and about 1.5 wt.-%.

Accordingly, a mixture of oil and water being in presence of gases and especially a mixture of hydrocarbons and water being in presence of hydrocarbon gases treated with a hydrate inhibitor composition according to the first aspect of the invention preferably comprises between about 0.001 wt.-% and about 4.0 wt.-% more preferably between about 0.005 wt.-% and about 1.5 wt.-%, and especially preferred between 0.01 wt.-% and about 0.50 wt.-% as for example between about 0.001 wt.-% and about 1.5 wt.-%, or between about 0.001 wt.-% and about 0.50 wt.-%, or between about 0.005 wt.-% and about 4.0 wt.-%, or between about 0.005 wt.-% and about 0.50 wt.-%, or between about 0.01 wt.-% and about 4.0 wt.-% or between about 0.01 wt.-% and about 1.5 wt.-% relative to the total weight of the aqueous phase of a composition according to the first aspect of the invention.

The contacting may be achieved by a number of ways, including mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition in the mixture. The contacting can be made in-line or batchwise or both. The various components of the composition may be mixed prior to or during contact, or both. If needed or desired, the composition or some of its components may be optionally removed or separated mechanically, chemically, or by other methods known to one skilled in the art, or by a combination of these methods after the hydrate formation conditions are no longer present.

Preferably, contacting of the hydrate inhibitor composition according to the invention with the mixture of gas and water is conducted prior to substantial formation of hydrates. More preferably it is conducted prior to the onset of hydrate formation. This may be at high temperatures as for example temperatures prevailing downhole, at low pressures and/or at low water-cuts.

The hydrate inhibitor composition may be introduced into the fluid comprising gas and water through a conduit or an injection point. In certain embodiments, the hydrate inhibitor composition may be introduced into a wellbore, a conduit, a vessel, and the like and may contact and/or be introduced into a fluid residing therein. An exemplary application point for the petroleum liquid production operations is to introduce hydrate inhibitor into the subsea wellhead itself, upstream of the well choke valve. This ensures that during a shut-in the composition can disperse throughout the area where natural gas hydrates have the highest risk of occurring. Application of the hydrate inhibitor composition can also occur at other areas in the wellhead or flowline manifold or the flowline itself, considering the density of the injected liquid. If the injection point is well above the gas hydrate formation depth, then the hydrate inhibitor composition may be formulated with a solvent having a density high enough that the composition will sink in the flowline to collect at the water/oil interface. In embodiments, application is also used in pipelines or anywhere in the system where the potential for agglomerates of gas hydrate formation exists.

The method according to the second aspect and the use according to the third aspect of the invention are equally applicable for fluids which are flowing as well as for fluids which are substantially stationary. Accordingly, the fluid may be within a vessel, or within a conduit (e.g., a conduit that may transport the fluid), or within a subterranean formation and/or a wellbore penetrating a portion of the subterranean formation. Examples of conduits include, but are not limited to, pipelines, production piping, subsea tubulars, process equipment, and the like as used in industrial settings and/or as used in the production of oil and/or gas from a subterranean formation, and the like. The conduit may in certain embodiments penetrate at least a portion of a subterranean formation, as in the case of an oil and/or gas well. In particular embodiments, the conduit may be a wellbore or may be located within a wellbore penetrating at least a portion of a subterranean formation. Such oil and/or gas well may, for example, be a subsea well (e.g., with the subterranean formation being located below the sea floor), or it may be a surface well (e.g., with the subterranean formation being located below ground). A vessel or conduit according to other embodiments may be located in an industrial setting such as a refinery (e.g., separation vessels, dehydration units, pipelines, heat exchangers, and the like), or it may be a transportation pipeline.

The method according to the second aspect and the use according to the third aspect of the present invention are particularly suitable for lower boiling hydrocarbons or hydrocarbon gases at ambient temperature when the pressure is at or greater than atmospheric pressure. (i.e. about 101 kPa), preferably greater than about 1 MPa, and more preferably greater than about 5 MPa. The pressure in certain formation or processing plants or units could be much higher, say greater than about 20 MPa. There is no specific high-pressure limit. The present method can be used at any pressure that allows formation of hydrocarbon gas hydrates. Lower temperatures tend to favor hydrate formation, thus requiring the treatment with the composition of the present invention; at much higher temperatures, however, hydrocarbon hydrates are less likely to form, thus obviating the need of carrying out any treatments.

For ease of handling, the hydrate inhibitor composition comprising as active ingredients an amphiphile (A), a cationic surfactant (B) and optionally a further surfactant (C), may be formulated with a diluent. Preferred diluents are generally solvents for the virgin form of the active ingredients. Such solvents include, but are not limited to monohydric alcohols having 1 to 12 carbon atoms like methanol, ethanol, n-propanol, iso-propanol, n-butanol, iso-butanol, tert-butanol, pentanol, hexanol, heptanol, octan-1-ol, octan-2-ol and 2-ethylhexan-1-ol; glycols like ethylene glycol, 1,2-propylene glycols, 1,3-propylene glycol, hexylene glycol and glycerol; ether solvents like ethylene glycol mono butylether (butyl cellosolve), ethylene glycol dibutyl ether, and tetrahydrofuran; ketonic solvents like acetone, methylethylketone, diisobutylketone, N-methylpyrrolidone, cyclohexanone; acetonitrile; esters such as ethyl acetate, propyl acetate and butyl acetate; and mixtures thereof. In a further preferred embodiment, a higher boiling aliphatic, aromatic or alkylaromatic hydrocarbon, or a mixture thereof has proven to be advantageous. Most preferred solvents are methanol, ethanol, glycerol, decane, toluene, xylene, diethylbenzene, naphthalene, tetralin, decalin, and commercial solvent mixtures such as Shellsol®, Exxsol®, Isopar®, Solvesso® types, diesel, Solvent Naphtha and/or kerosene. The more polar organic solvents like for example monohydric and polyhydric alcohols having 1 to 5 and especially having 1 to 3 carbon atoms may also be used in admixture with water, brine, and/or seawater. The selection of a suitable diluent or combination of diluents is important to maintain a stable solution of the compounds during storage and to provide stability and reduced viscosity for the inhibitor solutions when they are injected against a pressure of 200 to 30,000 psi. If a diluent is present in the formulation of the hydrate inhibitor composition, its concentration is preferably in the range of from about 1 to about 95 wt.-%, more preferably from about 10 to about 90 wt.-%, and especially preferred from about 20 to about 80%, as for example from about 1 to about 90 wt.-%, or from about 1 to about 80 wt.-%, or from about 10 to about 95 wt.-%, or from about 10 to about 80 wt.-%, or from about 20 to about 95 wt.-%, or from about 20 to about 90 wt.-%, based on the weight of the formulation comprising (A), (B), optionally (C) and the diluent. Such formulations can be delivered in subsea umbilicals.

In a preferred embodiment, finished product formulations are made to approximately 40 to 75 wt.-% as for example 60 wt.-% active content and 25 to 60 wt.-% as for example 40 wt.-% of a solvent. They are made as active as possible to save on space, logistics, and pump capacity which are all relevant concerns where treating production fluids offshore. However, often the maximum viscosity specified for a concrete application (commonly <100 cP at 4° C.) sets an upper limit.

The present invention may also be used in combination with other means of hydrate inhibition such as the use of thermodynamic or kinetic inhibitors discussed in the background section. These other hydrate inhibitors may be of the same or different type of hydrate inhibitor used in the composition. If mixtures of hydrate inhibitors are used, the mixture may be added to the hydrocarbon and water containing process stream through a single port or multiple ports. Alternatively, individual hydrate inhibitors may be added at separate ports to the process stream.

The present invention may also be used in combination with other oil field flow assurance and integrity compounds such as, but not limited to, corrosion inhibitors, scale inhibitors, paraffin inhibitors, asphaltene inhibitors, drilling fluids, fracturing fluids, completion fluids, antifoams, emulsion breakers, and/or water clarifiers.

EXAMPLES

Test Procedure 1: Evaluation of Hydrate Inhibitor Formulations.

To a 100 mL stainless steel reactor, attached to thermostat and a liquid handling system, dodecane (10 mL), brine (20 mL of 5% NaCl, density of 1.07 g/cm$^3$ at 25° C.), and the anti-agglomerant formulation were added at 30° C. The reactor was pressurized to 95 bar with Erdgas H (see Table 1 for composition). The stirrer speed was adjusted to 1000 rpm for 1 min to saturate the liquid with gas. Subsequently the stirrer speed was reduced to 200 rpm, and a temperature setting of 10° C. was initiated. Monitoring the internal temperature of the reactor showed a characteristic exotherm indicative of hydrate formation below a threshold temperature. If the exotherm was accompanied by a prolonged increase in stirrer power uptake this was indicative of agglomeration, signifying a failure. If the stirrer power remained constant or following an increase returned to the original baseline, agglomeration was prevented; indicating a pass.

For evaluation of their hydrate inhibitor performance, the testing was started with 0.3 wt.-% of the hydrate inhibitor, formulated as a 60% active solution in methanol. If samples failed at this dose rate, they were labeled as >0.3 wt.-% minimum effective dose (MED) and were not tested further. If samples initially tested at 0.3 wt.-% passed, they were sequentially and incrementally reduced in dose rate by 0.05 wt.-% each time until a dose rate was used that failed. When that occurred, the last passing dose rate was input into the Table (4) as the Minimum Effective Dose (MED).

TABLE 1

Erdgas H gas composition

| Component Name | Chemical Symbol | Amount (mol-%) |
|---|---|---|
| Nitrogen | $N_2$ | 0.14 |
| Carbon Dioxide | $CO_2$ | 0.00 |
| Methane | $C_1$ | 87.56 |
| Ethane | $C_2$ | 7.60 |
| Propane | $C_3$ | 3.00 |
| i-Butane | $i\text{-}C_4$ | 0.50 |
| n-Butane | $n\text{-}C_4$ | 0.80 |
| i-Pentane | $i\text{-}C_5$ | 0.20 |
| n-Pentane | $n\text{-}C_5$ | 0.20 |

Test Procedure 2: Water Drop Testing

Into a graduated 100 mL cylinder with conical bottom (typically used for emulsion testing), 50 mL of oil and 50 mL of water were charged. The water was 6% brine (using NaCl) and the oil was a medium crude from the Gulf of Mexico. To the 100 mL of total fluids 1 wt.-% in respect to the aqueous phase of a hydrate inhibitor (as a 60 wt.-% active formulation) were added. A dose rate of 1% was deliberately chosen to highlight the effect of the hydrate inhibitors on the water drop. The bottles were capped, shaken vigorously by hand, and allowed to stand at room temperature for 1 minute, at which point the amount of water that could be observed as a separate phase was recorded. This number was then multiplied by 2 to obtain the results shown in Table 4 as a percent of water present. A value of 100% means that all the water was observed as a separate phase. If less than 100% was observed, the remaining water was either within the oil or as part of a "rag layer" or emulsion layer.

For testing, gas hydrate inhibitor formulations were prepared by blending amphiphiles (A) according to table 2 and cationic surfactants (B) according to table 3 with the weight ratios according to table 4. For ease of handling, the formulations were adjusted to 60 wt.-% active content with methanol.

These formulations were tested for their minimum dosage rate for hydrate inhibition according to test procedure 1. The minimum dosage rates for a pass given in table 4 refer to the required minimum dosage of active ingredient.

TABLE 2

Characterization of tested amphiphiles A)

| Residue | A1 | A2 |
|---|---|---|
| L | $-N(R^7)-C(=O)-(CH_2)_2-N(R^6)-(CH_2)_t-$ | $-C(=O)-N(R^6)-(CH_2)_t-$ |
| $R^1$ | n-butyl | n-butyl |
| $R^2$ | n-butyl | n-butyl |
| $R^3$ | $C_2H_5$ | H |
| $R^5$ | $C_{12}H_{25}$ | coconut cut |
| $R^6$ | H | H |
| $R^7$ | H | — |
| t | 3 | 3 |
| $X^-$ | ethyl sulfate | acrylate |

| Residue | A3 | A4 |
|---|---|---|
| L | $-CH(OH)-CH_2-N(R^6)-(CH_2)_t-$ | 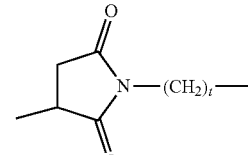 |
| $R^1$ | n-butyl | methyl |
| $R^2$ | n-butyl | methyl |
| $R^3$ | H | $-CH_2-CH(OH)-CH_3$ |
| $R^5$ | $C_{10}H_{21}$ | $C_{12}H_{25}$ |
| $R^6$ | H | — |
| $R^7$ | — | — |
| t | 3 | 3 |
| $X^-$ | methyl sulfate | acetate |

Coconut cut comprises as main components 51 wt.-% $C_{12}H_{25}$, and 16 wt.-% $C_{14}H_{29}$.

TABLE 3

Characterization of tested cationic surfactants B) having general formula $N^+(R^{11})(R^{12})(R^{19})(R^{29})\ Y^-$

| | $R^{11}$ | $R^{12}$ | $R^{19}$ | $R^{20}$ | $Y^-$ |
|---|---|---|---|---|---|
| B1 | coco alkyl | $CH_3$ | $CH_3$ | benzyl | $Cl^-$ |
| B2 | $C_8H_{17}$ | $CH_3$ | $CH_3$ | benzyl | $Cl^-$ |
| B3 | $C_{10}H_{21}$ | $CH_3$ | $CH_3$ | benzyl | $Cl^-$ |
| B4 | $C_{12}H_{25}$ | $CH_3$ | $CH_3$ | benzyl | $Cl^-$ |
| B5 | $C_{12}H_{25}$ | $CH_3$ | $CH_3$ | benzyl | $Br^-$ |
| B6 | $C_{14}H_{29}$ | $CH_3$ | $CH_3$ | benzyl | $Cl^-$ |
| B7 | $C_{16}H_{33}$ | $CH_3$ | $CH_3$ | benzyl | $Cl^-$ |
| B8 | $C_{18}H_{37}$ | $CH_3$ | $CH_3$ | benzyl | $Cl^-$ |
| B9 | iso-$C_{13}H_{27}$ | $CH_3$ | $C_2H_5$ | benzyl | ethyl sulfate |

TABLE 3-continued

Characterization of tested cationic surfactants B) having general formula $N^+(R^{11})(R^{12})(R^{19})(R^{29})$ $Y^-$

| | $R^{11}$ | $R^{12}$ | $R^{19}$ | $R^{20}$ | $Y^-$ |
|---|---|---|---|---|---|
| B10 | coco alkyl | $CH_3$ | coco alkyl | benzyl | $Br^-$ |
| B11 (comp.) | $C_{16}H_{33}$ | $CH_3$ | $CH_3$ | $CH_3$ | $Cl^-$ |
| B12 (comp.) | $C_{12}H_{25}$ | $CH_3$ | $CH_3$ | $C_4H_9$ | $Br^-$ |
| B13 (comp.) | $C_{16}H_{33}$ | $CH_3$ | $CH_3$ | $C_4H_9$ | $Br^-$ |
| B14 (comp.) | $C_{18}H_{37}$ | $CH_3$ | $CH_3$ | $C_4H_9$ | $Br^-$ |
| B15 (comp.) | $C_{10}H_{21}$ | $C_4H_9$ | $C_4H_9$ | $C_4H_9$ | $Br$ |
| B16 (comp.) | $C_{12}H_{25}$ | $H$ | $CH_3$ | $C_{12}H_{25}$ | $Cl^-$ |

Coco alkyl comprises as main components 51 wt.-% $C_{12}H_{25}$, and 16 wt.-% $C_{14}H_{29}$.

TABLE 4a

Results from autoclave testing (components testing; comparative)

| Example | Gas hydrate inhibitor (wt.-% active) comp. A | comp. B | MED (wt.-%) | water drop (%) |
|---|---|---|---|---|
| 1 (comp.) | A1 (100) | — | 0.30 | 80 |
| 2 (comp.) | A2 (100) | — | 0.30 | 84 |
| 3 (comp.) | A3 (100) | — | 0.30 | 76 |
| 4 (comp.) | A4 (100) | — | 0.30 | 74 |
| 5 (comp.) | — | B1 (100) | >0.30[a] | 58 |
| 6 (comp.) | — | B2 (100) | >0.30[a] | 62 |
| 7 (comp.) | — | B3 (100) | >0.30[a] | 60 |
| 8 (comp.) | — | B4 (100) | >0.30[a] | 60 |
| 9 (comp.) | — | B5 (100) | >0.30[a] | 56 |
| 10 (comp.) | — | B6 (100) | >0.30[a] | 62 |
| 11 (comp.) | — | B7 (100) | >0.30[a] | 64 |
| 12 (comp.) | — | B8 (100) | >0.30[a] | 60 |
| 13 (comp.) | — | B9 (100) | >0.30[a] | 54 |
| 14 (comp.) | — | B10 (100) | >0.30[a] | 60 |
| 15 (comp.) | — | B11 (100) | >0.30[a] | 64 |
| 16 (comp.) | — | B12 (100) | 0.30 | 70 |
| 17 (comp.) | — | B13 (100) | >0.30[a] | 76 |
| 18 (comp.) | — | B14 (100) | >0.30[a] | 70 |
| 19 (comp.) | — | B15 (100) | 0.30 | 72 |
| 20 (comp.) | — | B16 (100) | >0.30[a] | 70 |

[a] >0.30 wt.-% means it did not pass at 0.30 wt.-% dose rate and was not tested at higher concentration.

TABLE 4b

Results from autoclave testing (formulations containing A1)

| Example | Gas hydrate inhibitor (wt.-% active) comp. A | comp. B | MED (wt.-%) | water drop (%) |
|---|---|---|---|---|
| 21 | A1 (50.0) | B1 (50.0) | 0.10 | 86 |
| 22 | A1 (71.4) | B1 (28.6) | 0.05 | 88 |
| 23 | A1 (50.0) | B2 (50.0) | 0.15 | 88 |
| 24 | A1 (71.4) | B2 (28.6) | 0.10 | 88 |
| 25 | A1 (50.0) | B3 (50.0) | 0.10 | 86 |
| 26 | A1 (71.4) | B3 (28.6) | 0.10 | 90 |
| 27 | A1 (50.0) | B4 (50.0) | 0.10 | 86 |
| 28 | A1 (71.4) | B4 (28.6) | 0.05 | 88 |
| 29 | A1 (28.6) | B4 (71.4) | 0.10 | 86 |
| 30 | A1 (50.0) | B6 (50.0) | 0.10 | 88 |
| 31 | A1 (71.4) | B6 (28.6) | 0.05 | 92 |
| 32 | A1 (50.0) | B7 (50.0) | 0.10 | 88 |
| 33 | A1 (71.4) | B7 (28.6) | 0.05 | 88 |
| 34 | A1 (50.0) | B10 (50.0) | 0.15 | 86 |
| 35 | A1 (71.4) | B10 (28.6) | 0.15 | 86 |
| 36 (comp.) | A1 (50.0) | B14 (50.0) | 0.20 | 84 |
| 37 (comp.) | A1 (71.4) | B14 (28.6) | 0.20 | 84 |
| 38 (comp.) | A1 (50.0) | B15 (50.0) | 0.30 | 82 |
| 39 (comp.) | A1 (71.4) | B15 (28.6) | 0.25 | 84 |
| 40 (comp.) | A1 (50.0) | B16 (50.0) | >0.30[a] | 84 |
| 41 (comp.) | A1 (71.4) | B16 (28.6) | >0.30[a] | 84 |

TABLE 4c

Results from autoclave testing (formulations containing A2)

| Example | Gas hydrate inhibitor (wt.-% active) comp. A | comp. B | MED (wt.-%) | water drop (%) |
|---|---|---|---|---|
| 42 | A2 (50.0) | B1 (50.0) | 0.05 | 94 |
| 43 | A2 (71.4) | B1 (28.6) | 0.05 | 96 |
| 44 | A2 (28.6) | B1 (71.4) | 0.10 | 94 |
| 45 | A2 (50.0) | B2 (50.0) | 0.15 | 94 |
| 46 | A2 (71.4) | B2 (28.6) | 0.10 | 94 |
| 49 | A2 (50.0) | B4 (50.0) | 0.05 | 98 |
| 50 | A2 (71.4) | B4 (28.6) | 0.05 | 96 |
| 51 | A2 (50.0) | B5 (50.0) | 0.10 | 96 |
| 52 | A2 (71.4) | B5 (28.6) | 0.10 | 96 |
| 53 | A2 (80.0) | B6 (20.0) | 0.05 | 98 |
| 54 | A2 (50.0) | B6 (50.0) | 0.05 | 96 |
| 55 | A2 (20.0) | B6 (80.0) | 0.15 | 94 |
| 56 | A2 (50.0) | B7 (50.0) | 0.10 | 94 |
| 57 | A2 (71.4) | B7 (28.6) | 0.05 | 96 |
| 58 | A2 (50.0) | B9 (50.0) | 0.15 | 96 |
| 59 | A2 (71.4) | B9 (28.6) | 0.10 | 94 |
| 60 | A2 (50.0) | B10 (50.0) | 0.15 | 96 |
| 61 | A2 (71.4) | B10 (28.6) | 0.15 | 96 |
| 62 (comp.) | A2 (50.0) | B11 (50.0) | 0.30 | 90 |
| 63 (comp.) | A2 (71.4) | B11 (28.6) | 0.25 | 92 |
| 64 (comp.) | A2 (28.6) | B12 (71.4) | 0.20 | 90 |
| 65 (comp.) | A2 (50.0) | B12 (50.0) | 0.20 | 90 |
| 66 (comp.) | A2 (71.4) | B12 (28.6) | 0.25 | 88 |
| 67 (comp.) | A2 (50.0) | B13 (50.0) | 0.20 | 88 |
| 68 (comp.) | A2 (71.4) | B13 (28.6) | 0.20 | 86 |
| 69 (comp.) | A2 (50.0) | B16 (50.0) | 0.30 | 92 |
| 70 (comp.) | A2 (71.4) | B16 (28.6) | 0.25 | 92 |

TABLE 4d

Results from autoclave testing (formulations containing A3)

| Example | Gas hydrate inhibitor (wt.-% active) comp. A | comp. B | MED (wt.-%) | water drop (%) |
|---|---|---|---|---|
| 71 | A3 (50.0) | B3 (50.0) | 0.15 | 90 |
| 72 | A3 (71.4) | B3 (28.6) | 0.10 | 92 |
| 73 | A3 (50.0) | B4 (50.0) | 0.10 | 92 |
| 74 | A3 (71.4) | B4 (28.6) | 0.10 | 92 |
| 75 | A3 (50.0) | B6 (50.0) | 0.10 | 90 |
| 76 | A3 (71.4) | B6 (28.6) | 0.10 | 94 |
| 77 | A3 (50.0) | B7 (50.0) | 0.15 | 96 |
| 78 | A3 (71.4) | B7 (28.6) | 0.10 | 96 |
| 79 | A3 (50.0) | B8 (50.0) | 0.15 | 94 |
| 80 | A3 (71.4) | B8 (28.6) | 0.10 | 96 |
| 81 | A3 (50.0) | B9 (50.0) | 0.15 | 92 |
| 82 | A3 (71.4) | B9 (28.6) | 0.10 | 94 |
| 83 (comp.) | A3 (50.0) | B11 (50.0) | >0.30[a] | 86 |
| 84 (comp.) | A3 (71.4) | B11 (28.6) | 0.30 | 86 |
| 85 (comp.) | A3 (50.0) | B13 (50.0) | >0.30[a] | 84 |
| 86 (comp.) | A3 (71.4) | B13 (28.6) | >0.30[a] | 86 |
| 87 (comp.) | A3 (50.0) | B14 (50.0) | 0.20 | 88 |
| 88 (comp.) | A3 (71.4) | B14 (28.6) | 0.20 | 88 |

TABLE 4d-continued

Results from autoclave testing (formulations containing A3)

| Example | Gas hydrate inhibitor (wt.-% active) comp. A | comp. B | MED (wt.-%) | water drop (%) |
|---|---|---|---|---|
| 89 (comp.) | A3 (50.0) | B15 (50.0) | 0.25 | 84 |
| 90 (comp.) | A3 (71.4) | B15 (28.6) | 0.25 | 86 |

TABLE 4e

Results from autoclave testing (formulations containing A4)

| Example | Gas hydrate inhibitor (wt.-% active) comp. A | comp. B | MED (wt.-%) | water drop (%) |
|---|---|---|---|---|
| 91 | A4 (50.0) | B1 (50.0) | 0.10 | 84 |
| 92 | A4 (71.4) | B1 (28.6) | 0.10 | 86 |
| 93 | A4 (50.0) | B3 (50.0) | 0.15 | 84 |
| 94 | A4 (71.4) | B3 (28.6) | 0.10 | 84 |
| 95 | A4 (50.0) | B5 (50.0) | 0.15 | 86 |
| 96 | A4 (71.4) | B5 (28.6) | 0.10 | 88 |
| 97 | A4 (50.0) | B6 (50.0) | 0.15 | 86 |
| 98 | A4 (71.4) | B6 (28.6) | 0.15 | 90 |
| 99 | A4 (50.0) | B7 (50.0) | 0.15 | 88 |
| 100 | A4 (71.4) | B7 (28.6) | 0.10 | 88 |
| 101 | A4 (50.0) | B8 (50.0) | 0.15 | 86 |
| 102 | A4 (71.4) | B8 (28.6) | 0.10 | 90 |
| 103 | A4 (50.0) | B9 (50.0) | 0.15 | 88 |
| 104 | A4 (71.4) | B9 (28.6) | 0.10 | 88 |
| 105 (comp.) | A4 (50.0) | B12 (50.0) | 0.30 | 80 |
| 106 (comp.) | A4 (71.4) | B12 (28.6) | 0.25 | 82 |
| 107 (comp.) | A4 (50.0) | B13 (50.0) | 0.20 | 80 |
| 108 (comp.) | A4 (71.4) | B13 (28.6) | 0.20 | 82 |
| 109 (comp.) | A4 (50.0) | B16 (50.0) | >0.30(a) | 82 |
| 110 (comp.) | A4 (71.4) | B16 (28.6) | >0.30(a) | 80 |

(a)>0.30 wt.-% means it did not pass at 0.30 wt.-% dose rate and was not tested at higher concentration.

The invention claimed is:

1. A method for inhibiting the formation of gas hydrate agglomerates and plugs, the method comprising bringing a system containing hydrocarbons and water susceptible to gas hydrate formation into contact with a composition comprising
A) from 5 to 95 weight % of an amphiphile having a hydrophobic tail, $R^5$, linked to a hydrophilic head group $-N(R^1)(R^2)$ or $-[N(R^1)(R^2)(R^3)]^+X^-$ by a linking moiety, L,
the amphiphile having the general formula (1)

$[R^5\text{-L-}N(R^1)(R^2)(R^3)]^+X^-$ (1)

wherein each of $R^1$ and $R^2$ is independently an alkyl group having from 1 to 5 carbon atoms; or the nitrogen atom and the $R^1$ and $R^2$ groups together form a substituted or unsubstituted heterocyclic group;
$R^3$ is optionally present; when present, $R^3$ is hydrogen or an alkyl group having from 1 to 8 carbon atoms which optionally bears a hydroxy group or a carboxy group at the 2-position;
L comprises an optionally substituted hydrocarbyl group having at least 2 adjacent carbon atoms, at least one heteroatom selected from nitrogen and oxygen, and optionally one or more further heteroatoms;
$R^5$ is a hydrocarbyl group having from 6 to 22 carbon atoms;
X– is present as an anion when $R^3$ is present; and
B) from 5 to 95 weight-% of a cationic surfactant which is selected from the group consisting of quaternary benzyl ammonium salts having, in addition to the benzyl group, at least one $C_8$-$C_{18}$-alkyl group bound to the nitrogen atom.

2. The method according to claim 1, wherein the pressure during contacting is at or greater than atmospheric pressure.

3. The method according to claim 1, wherein the hydrocarbon is a naturally produced gas with the major part of the gas being $C_1$-$C_5$ hydrocarbons.

4. The method according to claim 1, wherein $R^1$ and $R^2$ independently are alkyl groups having from 3 to 5 carbon atoms.

5. The method according to claim 1, wherein $R^5$ is an alkyl or alkenyl group having between 8 and 20 carbon atoms.

6. The method according to claim 1, wherein $R^3$ is present as hydrogen or as a methyl group.

7. The method according to claim 1, wherein X– is selected from the group consisting of hydroxide, carboxylate, halide, sulphate, nitrite, nitrate, organic sulfonate, phosphate, organic phosphonate and combinations thereof.

8. The method according to claim 1, wherein X– is a carboxylate anion.

9. The method according to claim 8, wherein the carboxylate anion is selected from the group consisting of formate, acetate, propionate, acrylate, methacrylate and any combination thereof.

10. The method according to claim 1, wherein the linking moiety L contains a connecting chain that directly connects the hydrophilic head group to the hydrophobic tail, the connecting chain comprising: at least 2 adjacent carbon atoms, at least one heteroatom selected from nitrogen and oxygen, and, optionally, one or more additional heteroatoms, wherein the carbon atoms and heteroatoms are optionally substituted.

11. The method according to claim 10, wherein the connecting chain is an optionally substituted heteroaliphatic chain comprising at least one heteroatom selected from the group consisting of nitrogen and oxygen.

12. The method according to claim 11, wherein the at least one heteroatom is nitrogen.

13. The method according to claim 10, wherein the connecting chain is a heteroaliphatic chain wherein one or more non-adjacent $CH_2$ groups are replaced by a heteroatom selected from the group consisting of nitrogen and oxygen and optionally by one or more further heteroatom(s) which are part of a functional group selected from the group consisting of —C(=O)—O—, —O—C(=O)—, —C(=O)—NR$^6$—, —NR$^7$—C(=O), —NR$^6$—, —R$^7$N—, —O—, —S—, —(SO)— or —(SO$_2$)—, wherein $R^6$ is hydrogen or an alkyl group having from 1 to 5 carbon atoms, and $R^7$ is hydrogen or an organic moiety having from 1 to 20 carbon atoms.

14. The method according to claim 10, wherein the connecting chain comprises one or more aliphatic groups having 2 to 10 adjacent carbon atoms, connected
  a) to each other;
  b) to the hydrophobic tail; or
  c) to both a) and b)
by a heteroatom, wherein the heteroatom may be part of a functional group selected from the group consisting of —C(=O)—O—, —O—C(=O)—, —C(=O)—N(R$^6$)—, —N(R$^7$)—C(=O)—, —N(R$^6$)—, —(R$^7$)N—, —O—, —S—, —(SO)— of and —(SO$_2$)—, wherein $R^6$ is hydrogen or an alkyl group having from 1 to 5 carbon atoms and $R^7$ is hydrogen or an organic moiety having from 1 to 20 carbon atoms.

15. The method according to claim 1, wherein the structure of the linking moiety L corresponds to one out of formulae (2) to (12b)

$$—C(=O)—N(R^6)—(CH_2)_t— \quad (2)$$

$$—N(R^7)—C(=O)—(CH_2)_t— \quad (3)$$

$$—N(R^7)—(CH_2)_2—C(=O)—NH—(CH_2)_t— \quad (4)$$

$$—N(R^7)—C(=O)—(CH_2)_2—N(R^6)—(CH_2)_t— \quad (5)$$

$$—CH(OH)—CH_2—N(R^6)—(CH_2)_t— \quad (6)$$

$$—CH(COOH)—CH_2—C(=O)—N(R^6)—(CH_2)_t— \quad (7a)$$

$$—CH(CH_2—COOH)—C(=O)—N(R^6)—(CH_2)_t— \quad (7b)$$

(7c)

[structure: N-substituted succinimide ring with —(CH$_2$)$_t$— substituent]

$$—CH(COOH)—CH_2—C(=O)[O—(CH_2)_v]_v— \quad (8a)$$

$$—CH(CH_2—COOH)—C(=O)[O—(CH_2)_v]_v— \quad (8b)$$

$$—N(R^7)—C(=O)—(CH_2)_2—C(=O)—N(R^6)—(CH_2)_t— \quad (9)$$

$$—N(R^7)—C(=O)—CH_2—CH(OH)—C(=O)—N(R^6)—(CH_2)_t— \quad (10a)$$

$$—N(R^7)—C(=O)—CH(OH)—CH_2—C(=O)—N(R^6)—(CH_2)_t— \quad (10b)$$

$$—N(R^7)—C(=O)—CH(OH)—CH(OH)—C(=O)—N(R^6)—(CH_2)_t— \quad (11)$$

$$—N(R^7)—C(=O)—C(OH)(CH_2COOH)—CH_2—C(=O)—N(R^6)—(CH_2)_t— \quad (12a)$$

$$—N(R^7)—C(=O)—CH_2—C(OH)(CH(COOH)—C(=O)—N(R^6)—(CH_2)_t— \quad (12b)$$

wherein
t is 2, 3 or 4:
v is an integer between 1 and 30
$R^6$ is hydrogen or an alkyl group having from 1 to 5 carbon atoms; and
$R^7$ is hydrogen or an organic moiety having from 1 to 20 carbon atoms.

16. The method according to claim 1, wherein the amphiphile is an amido amine according to the general formula (13)

$$\left[ R^5 - \underset{R^8}{\overset{R^7}{N}} - \left[ CH_2 \right]_m - \underset{}{\overset{O}{\underset{\|}{C}}} - \left[ CH_2 \right]_o - \underset{R^6}{\overset{R^9}{N}} - R^4 - \underset{R^3}{\overset{R^1}{N}} - R^2 \right]^{q+}_n [X^-]_q \quad (13)$$

wherein
$R^1$, $R^2$, $R^3$, $R^5$ and X– have the general meanings given above for formula (1);
$R^4$ is selected from the group consisting of —(CH$_2$)$_t$—, —[(CH$_2$—CHR$^{10}$)]—, —(CH$_2$—CHR$^{10}$O)$_u$(CH$_2$)$_t$— and combinations thereof;
$R^6$ is hydrogen or an alkyl group having from 1 to 5 carbon atoms;
$R^7$ is hydrogen or an organic moiety having from 1 to 20 carbon atoms;
$R^8$ is present or not as hydrogen or an alkyl group having from 1 to 5 carbon atoms; with the proviso that when m=0, $R^8$ is not present;
$R^9$ is present or not as hydrogen or an alkyl group having from 1 to 5 carbon atoms; with the proviso that when o=0, $R^9$ is not present;
$R^{10}$ is an alkyl group having 1 to 4 carbon atoms;
m is 0 or 2,
n is 0 or 1,
o is 0 or 2,
p is 0 or an integer between 1 and 5;
q is 0 or an integer between 1 and 6, but is not more than the sum of n+p
n+p is an integer between 1 and 6;
s is 1, 2 or 3;
t is 2, 3 or 4; and
u is an integer between 1 and 100.

17. The method according to claim 1, wherein the amphiphile is an amido amine according to the general formula (14)

$$\left[ R^5 - \underset{R^6}{\overset{O}{\underset{\|}{C}}} - \underset{}{N} - R^4 \right]_p - \underset{R^3}{\overset{R^1}{N}} - R^2 \right]^{q+} (X^-)_q \quad (14)$$

wherein
$R^1$, $R^2$, $R^3$, $R^5$ and X– have the general meanings given above;
$R^4$ is selected from the group consisting of —(CH$_2$)$_t$— and —[(CH$_2$—CHR$^{10}$)$_s$]—;
$R^6$ is hydrogen or an alkyl group having from 1 to 5 carbon atoms;
$R^{10}$ is an alkyl group having 1 to 4 carbon atoms;
p is an integer between 1 and 5;
s is 1, 2 or 3;
t is 2, 3 or 4;
q is 0 when $R^3$ is absent, or q is 1 when $R^3$ is present.

18. The method according to claim 17, wherein the compound according to formula (14) is the reaction product of an N,N-dialkyl-aminoalkylamine of formula HN(R$^6$)—R$^4$—N(R$^1$)(R$^2$) with a fatty acid, a fatty acid ester or a glyceride.

19. The method according to claim 17, wherein the compound according to formula (14) includes a product prepared by the reaction of an amine selected from the group consisting of (3-dialkylamino)propylamine and (3-dialkylamino)ethylamine with a vegetable oil or tallow oil, followed by either neutralization with an acid selected from the group consisting of mineral acids and carboxylic acids having from 1 to 20 carbon atoms, or followed by quaternization with an alkylating agent selected from the group consisting of an organic halide, dimethyl sulfate, diethyl sulfate and $C_2$-$C_4$ alkylene oxides, and wherein the dialkyl amino group of the (3-dialkylamino)propylamine includes two alkyl groups independently selected from the group consisting of methyl, ethyl, propyl, butyl, and combinations thereof or, wherein $R^1$ and $R^2$ together with the nitrogen atom to which they are attached form a substituted or unsubstituted heterocyclic group having 5 or 6 atoms in the ring.

20. The method according to claim 1, wherein the amphiphile is an amido amine according to one or more of formulae (15), (16) and (17):

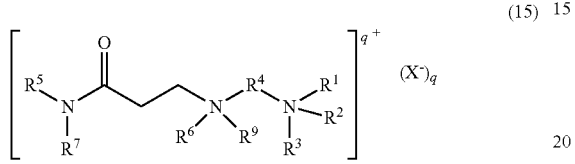
(15)

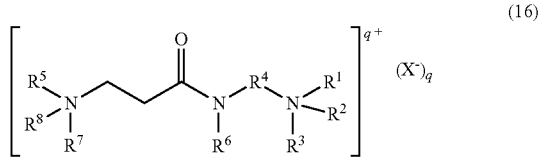
(16)

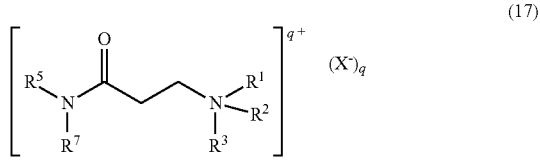
(17)

wherein $R^1, R^2, R^3, R^5$ and X– have the meanings given above for formula (1);

$R^4$ is —$(CH_2)_t$—;

$R^6$ is hydrogen or an alkyl group having from 1 to 5 carbon atoms;

$R^7$ is hydrogen or an organic moiety having 1 to 20 carbon atoms;

$R^8$ and $R^9$ independently is present or not as hydrogen or an alkyl group having from 1 to 5 carbon atoms;

q is 0 when $R^3$, $R^8$ and $R^9$ are absent; and q is 1, 2 or 3 depending on the presence of one or more of $R^3$, $R^8$ and $R^9$; and t is 2, 3 or 4.

21. The method according to claim 1, wherein the cationic surfactant is a benzyl ammonium compound of the formula (19):

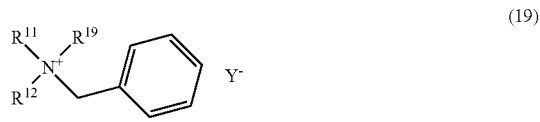
(19)

wherein $R^{11}$ is an alkyl group having 8 to 18 carbon atoms, $R^{12}$ is an alkyl group having from 1 to 5 carbon atoms, $R^{19}$ is an alkyl group having from 1 to 18 carbon atoms, and Y– is an anion.

22. The method according to claim 21, wherein $R^{12}$ and $R^{19}$ are methyl groups.

23. The method according to claim 21, wherein Y– is selected from the group consisting of, chloride, bromide, hydroxide, methosulfate, ethosulfate and combinations thereof.

24. The method according to claim 1, wherein the portion of the cationic surfactant is between 10 and 85 wt. % based on the combined weights of the amphiphile and the cationic surfactant.

25. The method according to claim 1, wherein the weight ratio between the amphiphile and the cationic surfactant is between 20:1 and 1:20.

26. The method according to claim 1, additionally containing up to 30 wt. % of a further surfactant being different from the amphiphile and the cationic surfactant, based on the combined masses of the amphiphile and the cationic surfactant.

27. The method according to claim 1, containing 1 to 30 wt. % of at least one further surfactant being different from the amphiphile and the cationic surfactant, wherein the at least one further surfactant is selected from the group consisting of anionic, nonionic, amphoteric and/or cationic surfactants.

28. The method according to claim 26, wherein the composition further comprises at least one kinetic gas hydrate inhibitor being different from the amphiphile, the cationic surfactant, and the at least one further surfactant.

29. The method according to claim 1, wherein the composition further comprises at least one diluent.

30. The method according to claim 29, wherein the diluent is selected from the group consisting of monohydric lower alcohols, glycols, ether solvents, ketonic solvents, esters, acetonitrile, water, aliphatic, aromatic, alkylaromatic solvents, and mixtures thereof.

31. The method according to claim 28, wherein the composition further comprises at least one diluent and wherein the diluent is present in the range from 0.1 wt. % to 95 wt. %, based on the combined weight of the amphiphile, the cationic surfactant, the at least one further surfactant and the diluent.

* * * * *